US006657103B1

(12) United States Patent
Kucherlapati et al.

(10) Patent No.: US 6,657,103 B1
(45) Date of Patent: *Dec. 2, 2003

(54) HUMAN ANTIBODIES DERIVED FROM IMMUNIZED XENOMICE

(75) Inventors: Raju Kucherlapati, Darien, CT (US); Aya Jakobovits, Menlo Park, CA (US); Sue Klapholz, Stanford, CA (US); Daniel G. Brenner, San Mateo, CA (US); Daniel J. Capon, Hillsborough, CA (US)

(73) Assignee: Abgenix, Inc., Fremont, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/923,138

(22) Filed: Sep. 4, 1997

Related U.S. Application Data

(63) Continuation of application No. 08/430,938, filed on Apr. 27, 1995, now abandoned, which is a continuation-in-part of application No. 08/234,145, filed on Apr. 28, 1994, now abandoned, which is a continuation-in-part of application No. 08/112,848, filed on Aug. 27, 1993, now abandoned, which is a continuation of application No. 08/031,801, filed on Mar. 15, 1993, which is a continuation-in-part of application No. 07/919,297, filed on Jul. 24, 1992, now abandoned, which is a continuation-in-part of application No. 07/610,515, filed on Nov. 8, 1990, now abandoned, which is a continuation-in-part of application No. 07/466,008, filed on Jan. 12, 1990, now abandoned.

(51) Int. Cl.[7] .................. C12P 21/00; A01K 67/027; C12N 15/63

(52) U.S. Cl. ................ 800/6; 800/4; 800/18; 435/320.1

(58) Field of Search ................ 800/4, 6, 18; 435/320.1

(56) References Cited

U.S. PATENT DOCUMENTS

| 4,816,397 | A |   | 3/1989  | Boss et al. ............... 435/68 |
|-----------|---|---|---------|------------------------------------|
| 4,950,599 | A |   | 8/1990  | Bertling ............... 435/172.3 |
| 4,959,313 | A |   | 9/1990  | Taketo ................. 435/69.1   |
| 5,204,244 | A |   | 4/1993  | Fell et al. ............. 435/69.6  |
| 5,545,806 | A | * | 8/1996  | Lonberg et al. .......... 800/2     |
| 5,545,807 | A | * | 8/1996  | Surani et al. ........... 800/2     |
| 5,569,824 | A |   | 10/1996 | Donehower et al. ....... 800/2      |
| 5,569,825 | A |   | 10/1996 | Lonberg et al. .......... 800/2     |
| 5,591,669 | A | * | 1/1997  | Krimpenfort ............. 800/2     |
| 6,150,584 | A | * | 11/2000 | Kucherlapati et al. ..... 800/18    |

FOREIGN PATENT DOCUMENTS

| AU | B-15172/95   | 7/1995  |
|----|--------------|---------|
| EP | 0 298 807 A1 | 6/1988  |
| EP | 0 315 062    | 5/1989  |
| EP | 0 322 240    | 6/1989  |
| EP | 322240       | 6/1989  |
| EP | 0 459 372 A3 | 5/1991  |
| EP | 0 463 151    | 1/1992  |
| WO | WO 90/04036  | 4/1990  |
| WO | WO 91/00906  | 1/1991  |
| WO | WO 91/10741  | 7/1991  |
| WO | WO 92/03918  | 3/1992  |
| WO | WO 93/05165  | 3/1993  |
| WO | WO 94/00569  | 1/1994  |
| WO | WO 94/02602  | 2/1994  |
| WO | WO 96/33735  | 10/1996 |

OTHER PUBLICATIONS

Bruggeman et al. *PNAS* 82: 6709, 1989.*
Cox, declaration in 5, 545, 806.*
Dorfman, Nickolas A., 1985, "The Optimal Technological Approach to the Development of Human Hybridomas," *Journal of Biological Response Modifiers* 4:213–239.
Taggart et al., 1983, "Stable Antibody–Producing Murine Hybridomas," *Science* 219:1228–1230.
Albertsen, et al., Construction and characterization of a yeast artificial chromosome library containing seven haploid human genome equivalents, *Proc. Natl. Acad. Sci.* 87:4256–4260 (1990).
Aldhous, "Transgenic mice display a class (switching) act," *Science* 262:1212–1213 (1993).
Ayares, et al., "Sequence homology requirements for intermolecular recombination in mammalian cells," *Proc. Natl. Acad. Sci.*, 83:5199–5203 (1986).
Berman, et al., "Content and organization of the human Ig $V_H$ locus: definition of three new $V_H$ families and linkage to the Ig $C_H$ locus," *EMBO J.*, 7:727–738 (1988).
Bird, et al., "Single–Chain Antigen–Binding Proteins," *Science*, 423–426 (1988).
Blankenstein, et al., "Immunoglobulin $V_H$ region genes of the mouse are organized in overlapping clusters," *Eur. J. Immunol.*, 17:1351–1357 (1987).
Brinster, et al., "Introns increase transcriptional efficiency in transgenic mice," *Proc. Natl. Acad. Sci.*, 85:836–840 (1988).
Brownstein, et al., "Isolation of single–copy human genes from a library of yeast artificial chromosome clones," *Science*, 244:1348–1351 (1989).
Brüggeman, et al., "Human antibody production in transgenic mice: expression from 100kb of th human IgH locus," *European Journal of Immunology*, 21:1323–1326 (1991).
Brüggemann, et al., "Construction, function and immunogenicity of recombinant monoclonal antibodies," *Behring Inst. Mitt.*, 87:21–24 (1990).

(List continued on next page.)

Primary Examiner—Anne M. Wehbe'
(74) Attorney, Agent, or Firm—Fish & Neave; James F. Haley, Jr.; Jane T. Gunnison

(57) ABSTRACT

Antibodies with fully human variable regions against a specific antigen can be prepared by administering the antigen to a transgenic animal which has been modified to produce such antibodies in response to antigenic challenge, but whose endogenous loci have been disabled. Various subsequent manipulations can be performed to obtain either antibodies per se or analogs thereof.

4 Claims, 18 Drawing Sheets

OTHER PUBLICATIONS

Burke, et al., "Cloning of large segments of exogenous DNA into yeast by means of artificial chromosome vectors," *Science*, 236:806–812 (1987).

Buttin, G., "Exogenous Ig gene rearrangement in transgenic mice: a new strategy for human monoclonal antibody production?," *Trends in Genetics*, 3(8):205–206 (1987).

Capecchi, et al., "Altering the Genome by Homologous Recombination," *Science*, 244(16):1288–1292 (1989).

Choi, et al., "Transgenic mice containing a human heavy chain immunoglobulin gene fragment cloned in a yeast artificial chromosome," *Nature Genetics* 4:117–123 (1993).

Choi et al., "RNA Splicing Generates a Variant Light Chain from an Aberrantly Arranged κ Gene," *Nature*, 286:776–779 (1980).

Davies, et al., "Targeted alterations in yeast artificial chromosomes for inter-species gene transfer," *Nuc. Acids Res.*, 20:2693–2698 (1992).

Doelker, et al., "The CySF–L2 factor from dialysable human leucocyte extract activates natural killer cytotoxicity by induction of interferon γ," *Cancer Immunology Immunotherapy*, 34:299–305 (1992).

Doetschman et al., "Targeted Mutation of the Hprt Gene in Mouse Embryonic Stem Cells," *Proc. Natl. Acad. Sci. USA*, 85:8583–8587 (1988).

Eisen, Herman N., "Immunology: An introduction to Molecular and Cellular Principles of the immune Responses," 349–351 (2d ed. 1989).

Eliceiri, et al., "Stable integration and expression in mouse cells of yeast artificial chromosomes harboring human genes," *Proc. Natl. Acad. Sci.*, 88:2179–2183 (1991).

Emery, et al., "Humanised monoclonal Antibodies for Therapeutic Applications," *Expert Opinion on Investigational Drugs*, 3:241–251 (1994).

Garza, et al., "Mapping the Drosophila genome with yeast artificial chromosomes," *Science*, 246:641–646 (1989).

Gnirke, et al., "Cloning and in vivo expression of the human GART gene using yeast artificial chromosomes," *EMBO*, 10(7):1629–1634 (1991).

Green et al., "Antigen-specific Human Monoclonal Antibodies from Mice Engineered with Human Ig Heavy and Light Chain Yacs," *Nature Genet.*, 7:13 (1994).

Griffiths, et al., "Isolation of high affinity human antibodies directly from large synthetic repertoires," *The EMBO Journal*, 13:3245–3260 (1994).

Huxley, et al., "The Human HPRT gene on a yeast artificial chromosome is functional when transferred to mouse cells by cell fusion," *Genomics*, 9:742–750 (1991).

Jakobovits et al., "Germ-line Transmission and Expression of a Human-derived Yeast Artificial Chromosome," *Nature*, 362:252–258 (1993).

James, et al., "Human monoclonal antibody production: current status and future prospects," *Journal of Immunological Methods*, 100:5–40 (1987).

Johnson et al., "Targeting of Nonexpressed Genes in Embryonic Stem Cells via Homologous Recombination," *Science*, 245:1234–1236 (1989).

Joyner, et al., "Productin of a mutation in mouse En–2 gene by homologous recombination in embryonic stem cells," *Nature*, 338:153–155 (1989).

Koller, et al., "Inactivating the $β_2$–microglobulin locus in mouse embryonic stem cells by homologous recombination," *Proc. Natl. Acad. Sci.*, 86:8932–8935 (1989).

Kucherlapati, R., "Homologous recombination in mammalian somatic cells," *Prog Nucleic Acid Res. Mol. Biol.*, 36:301–310 (1989).

Lenz, et al., "Expression of heterobispecific antibodies by genes transferred into producer hybridoma cells," *Gene*, 87:213–218 (1990).

Liu et al., "Chimeric mouse–human IgG1 antibody that can mediate lysics of cancer cells," *Proc Natl Acad Sci USA*, 84:3439–3443 (1987).

Mansour, et al., "Disruption of the proto–oncogene int–2 in mouse embryo–derived stem cells: a general strategy for targeting mutations to non–selectable genes," *Nature*, 336:348–352 (1988).

Matsuda, et al., "Structure and physical map of 64 variable segments in the 3' 0.8–megabase region of the human immunoglobulin heavy–chain locus," *Nature Genetics*, 3:88–94 (1993).

Max et al., "Sequences of Five Potential Recombination Sites Encoded Close to an Immunoglobulin K Constant Region Gene," *Proc. Natl. Acad. Sci. USA*, 76:3450–3454 (1979).

Miller, et al., "Structural alterations in J regions of mouse immunoglobulin lambda genes are associated with differential gene expression," *Nature*, 295:428–430 (1982).

Morrison et al., "Success Is in the Specification," *Nature*, 368:812–813 (1994).

Mortensen, et al., "Production of homozygous mutant ES cells with a single targeting construct," *Mol. Cell. Biol.*, 12(5):2391–2395 (1992).

Munker, et al., "Recombinant human TNF induces production of granulocyte–monocyte colony–stimulating factor," *Nature*, 323:79–82 (1986).

Orkin et al., "Mutation in an Intervening Sequence Splice Junction in Man," *Proc. Natl. Acad. Sci. USA*, 78:5041–5045 (1981).

Pachnis, et al., "Transfer of a yeast artificial chromosome carrying human DNA from *Saccharomyces cerevisiae* into mammalian cells," *Proc. Natl. Acad. Sci.*, 87:5109–5113 (1990).

Pavan, et al., "Modification and transfer into an embryonal carcinoma cell line of a 360–kilobase human–derived yeast artificial chromosome," *Mol. Cell. Biol.*, 10(8):4163–4169 (1990).

Queen, et al., "A humanized antibody that binds to the interleukin 2 receptor," *Proc. Natl. Acad. Sci. USA*, 86:10029–10033 (1989).

Rajewsky et al., "Evolutionary and Somatic Selection of the Antibody Repertoire in the Mouse," *Science*, 238:1088–1094 (1987).

Ramirez–Solis et al., "Chromosome Engineering in Mice," *Nature*, 378:720–724 (1995).

Sakano, et al., "Identification and nucleotide sequence of a diversity DNA segment (D) of immunoglobulin heavy––chain genes", *Nature*, 290:562–565 (1981).

Sakano, et al., "Two Types of Somatic Recombination are Necessary for the Generation of Complete Immonoglobulin Heavy–Chain Genes," *Nature* 286:676–683 (1980).

Sakano, et al., "Sequences at the Somatic Recombination Sites of Immunoglobulin Light–chain Genes," *Nature*, 280–294 (1979).

Schedl, et al., "A Method for the Generation of YAC Transgenic Mice by Pronuclear Microinjection," *Nucleic Acids Research* 21(20):4783–4787 (1993).

Schedl, et al., "A yeast artificial chromosome covering the tyrosine gene confers copy number–dependent expression in transgenic mice," *Nature*, 362:258–261 (1993).

Schedl, et al., "Transgenic Mice Generated by Pronuclear Injection of a Yeast Artificial Chromosome," *Nucleic Acids Res.*, 20:3073–3077 (1992).

Schwartzberg et al., "Germ–line Transmission of a c–abl Mutation Produced by Targeted Gene Disruption in ES Cells," *Science*, 246:799–803 (1989).

Seidman, et al., "A Mutant Immunoglobulin Light Chain Is Formed by Aberrant DNA–and RNA–Splicing Events," *Nature*, 286:779–783 (1980).

Shimizu, et al., "Immunoglobulin double–isotype expression by trans–mRNA in a human immunoglobulin transgenic mouse," *Proc. Natl. Acad. Sci.*, 86:8020–8023 (1989).

Shin, et al., "Physical map of the 3' region of the human immunoglobulin heavy chain locus: clustering of autoantibody–related variable segments in one haplotype," *EMBO J*, 10:3641–3645 (1991).

Strauss, et al., "Germ Line Transmission of a Yeast Artificial Chromosome Spanning the Murine $\alpha_1(1)$ Collagen Locus," *Science* 259:1904–1907 (1993).

Thomas, et al., "Site–directed metagenesis by gene targeting in mouse embryo–derived stem cells," *Cell*, 51:503–512 (1987).

Traver, et al., "Rapid screening of a human genomic library in yeast artificial chromosomes for single–copy sequences," *Proc. Natl. Acad. Sci.*, 86:5898–5902 (1989).

Treisman et al., "Specific Transcription and RNA Splicing Defects in Five Cloned β–thalessaemia Genes," *Nature*, 302:591–596 (1983).

Tucker, et al., "Mouse IgA heavy chain gene sequence: implications for evolution of immunoglobulin hinge exons," *Proc. Natl. Acad. Sci.*, 78:7684–7688 (1981).

Yancoupolos, et al. "Developmentally Controlled and Tissue–Specific Expression of Unrearranged $V_H$ Gene Segments," *Cell* 40:271–281 (1985).

Zachau, "The human immunoglobulin κ locus and some of its acrobatics," *Biol. Chem.*, 371:1–6 (1990).

Zjilstra et al., "Germ–line Transmission of a Disrupted β2–microglobulin Gene Produced by Homologous Recombination in Embryonic Stem Cells," *Nature*, 342:435–438 (1989).

Yamaura et al., "Cell–Type–Specific and Regulated Expression of a Human γ1 Heavy–Chain Immonoglobulin Gene in Transgenic Mice", *Proc. Natl. Acad. Sci., USA* 83:2152–2156 (1986).

* cited by examiner

FIG. 18A

|  | CDR1 | | | | 50 |
|---|---|---|---|---|---|
| Germline VH6 | AGACCCTCTC | ACTCACCTGT | GCCATCTCCG | GGGACAGTGT | CTCTAGCAAC |
| Hybridoma D5.1.4 | AGACCCTCTC | ACTCACCTGT | GCCATCTCCG | GGGACAGTGT | CTCTAGCGAC |
| Germline JH4 | ---------- | ---------- | ---------- | ---------- | ---------- |
| Germline D(N1) | ---------- | ---------- | ---------- | ---------- | ---------- |
| Germline hMu | ---------- | ---------- | ---------- | ---------- | ---------- |
|  |  | ←——— VH6 ———  | | | |

|  | | CDR2 | | | 100 |
|---|---|---|---|---|---|
| Germline VH6 | AGTGCTGCTT | GGAACTGGAT | CAGGCAGTCC | CCATCGAGAG | GCCTTGAGTG |
| Hybridoma D5.1.4 | AGTGCTGCTT | GGAACTGGAT | CAGGCAGTCC | CCATCGAGAG | GCCTTGAGTG |
| Germline JH4 | ---------- | ---------- | ---------- | ---------- | ---------- |
| Germline D(N1) | ---------- | ---------- | ---------- | ---------- | ---------- |
| Germline hMu | ---------- | ---------- | ---------- | ---------- | ---------- |
|  |  |  |  | ——— VH6 ———→ | |

|  | | | | | 150 |
|---|---|---|---|---|---|
| Germline VH6 | GCTGGGAAGG | ACATACTACA | GGTCCAAGTG | GTATAATGAT | TATGCAGTAT |
| Hybridoma D5.1.4 | GCTGGGAAGG | ACATACTACA | GGTCCAAGTG | GTATAATGAT | TATGCAGTTT |
| Germline JH4 | ---------- | ---------- | ---------- | ---------- | ---------- |
| Germline D(N1) | ---------- | ---------- | ---------- | ---------- | ---------- |
| Germline hMu | ---------- | ---------- | ---------- | ---------- | ---------- |
|  | ←——— VH6 ———  | | | | |

|  | | | | | 200 |
|---|---|---|---|---|---|
| Germline VH6 | CTGTGAAAAG | TCGAATAACC | ATCAACCCAG | ACACATCCAA | GAACCAGTTC |
| Hybridoma D5.1.4 | CTGTGAAAAG | TCGAATAACC | ATCAACCCAG | ACACATCCAA | GAACCAGTTC |
| Germline JH4 | ---------- | ---------- | ---------- | ---------- | ---------- |
| Germline D(N1) | ---------- | ---------- | ---------- | ---------- | ---------- |
| Germline hMu | ---------- | ---------- | ---------- | ---------- | ---------- |
|  | ←——— VH6 ———  | | | | |

FIG. 19A

```
Germline B3      GACATCGTGA TGACCCAGTC TCCAGACTCC CTGGCTGTGT CTCTGGGCGA
Hybridoma D5.1.4 ---------- ---------- ---------- ---------- ----------
Germline JK3
Germline CK CDR 1
Germline B3      GAGGGCCACC ATCAACTGCA AGTCCAGCCA GAGTGTTTTA TACAGCTCCA
Hybridoma D5.1.4 ---ACC---- ATCAACTGCA AGTCCAGCCA GAGTGTTTTG TACACTTCCA
Germline JK3                                             B3
Germline CK Germline B3      ACAATAAGAA CTACTTAGCT TGGTACCAGC AGAAACCAGG ACAGCCTCCT
Hybridoma D5.1.4 GCAATAAGAA CTACTTAGCT TGGTACCAGC AGAAACCAGG ACAGCCTCCT
Germline JK3            B3
Germline CK CDR2
Germline B3      AAGCTGCTCA TTTACTGGGC ATCTACCCGG GAATCCGGGG TCCCTGACCG
Hybridoma D5.1.4 AAACTACTCA TTTACTGGGC ATCTACCCGG GAATCCGGGG TCCCTGACCG
Germline JK3                                        B3
Germline CK Germline B3      ATTCAGTGGC AGCGGGGTCTG GGACAGATTT CACTCTCACC ATCAGCAGCC
Hybridoma D5.1.4 ATTCAGTGGC AGCGGGGTCTG GGACAGATTT CACTCTCACC ATCCGCAGCC
Germline JK3                                                  B3
Germline CK
```

FIG. 19B

```
Germline B3      TGCAGGCTGA AGATGTGGCA GTTTATTACT GTCAGCAATA TTATAGTACT
Hybridoma D5.1.4 TGCAGGCTGA AGATGTGGCA GTTTATTACT GTCAGCAATA TTATAGTACT
Germline JK3     ---------- ---------- ---------- ---------- ----------
Germline CK      ---------- ---------- ---------- ---------- ----------
                                              —————B3———————>

Germline B3      CC-------- ---------- ---------- ---------- ----------
Hybridoma D5.1.4 CCATTCAATT TCGGCCCTGG GACCAGAGTG GATATCAAAC GAACTGTGGC
Germline JK3     --ATTCACTT TCGGCCCTGG GACCAAAGTG GATATCAAAC
Germline CK                                                  GAACTGTGGC
                        <———————JK3——————————>         <————CK————

Germline B3      ---------- ---------- ---------- ---------- ----------
Hybridoma D5.1.4 TGCACCATCT GTCTTCATCT TCCCGCCATC TGATGAGCAG TTGAAATCTG
Germline JK3     ---------- ---------- ---------- ---------- ----------
Germline CK      TGCACCATCT GTCTTCATCT TCCCGCCATC TGATGAGCAG TTGAAATCTG
                                                                      CK Germline B3      ---------- ---------- ---------- ---------- ----------
Hybridoma D5.1.4 GAACTGCCTC TGTTGTGTGC CTGCTGAATA ACTTCTATCC CAGAGAGGCC
Germline JK3     ---------- ---------- ---------- ---------- ----------
Germline CK      GAACTGCCTC TGTTGTGTGC CTGCTGAATA ACTTCTATCC CAGAGAGGCC
                                                                      CK Germline B3      ---------- ---------- ---------- ---------- ----------
Hybridoma D5.1.4 AAAGTACAGT GGAAGGTGGA TAACGCCCTC CAATCGGGGT GGGGAAAAA
Germline JK3     ---------- ---------- ---------- ---------- ----------
Germline CK      AAAGTACAGT GGAAGGTGGA TAACGCCCTC CAATCGGGT- ---------
                                                                      CK
```

HUMAN ANTIBODIES DERIVED FROM IMMUNIZED XENOMICE

This application is a continuation of application Ser. No. 08/430,938, filed Apr. 27, 1995, now abandoned, which is a continuation-in-part of application Ser. No. 08/234,145, filed Apr. 28, 1994, now abandoned, which is a continuation-in-part of application Ser. No. 08/112,848, filed Aug. 27, 1993, now abandoned, which is a continuation of pending application Ser. No. 08/031,801, filed Mar. 15, 1993, which is a continuation-in-part of application Ser. No. 07/919,297, filed Jul. 24, 1992, now abandoned, which is a continuation-in-part of application Ser. No. 07/610,515, filed Nov. 8, 1990, now abandoned, which is a continuation-in-part of application Ser. No. 07/466,008, filed Jan. 12, 1990, now abandoned.

TECHNICAL FIELD

The invention relates to the field of immunology, and in particular to the production of antibodies. More specifically, it concerns producing such antibodies by a process which includes the step of immunizing a transgenic animal with an antigen to which antibodies are desired. The transgenic animal has been modified so as to produce human, as opposed to endogenous antibodies.

BACKGROUND ART

PCT application WO 94/02602, published Feb. 3, 1994 and incorporated herein by reference, describes in detail the production of transgenic nonhuman animals which are modified so as to produce antibodies with fully human variable regions rather than endogenous antibodies in response to antigenic challenge. Briefly, the endogenous loci encoding the light and heavy immunoglobulin chains are incapacitated in the transgenic hosts and loci encoding human heavy and light chain proteins are inserted into the genome. In general, the animal which provides all the desired modifications is obtained by cross-breeding intermediate animals containing fewer than the full complement of modifications. The preferred embodiment of the nonhuman animal described in the specification is a mouse. Thus, mice, specifically, are described which, when administered immunogens, produce antibodies with human variable regions, including fully human antibodies, rather than murine antibodies that are immunospecific for these antigens.

The availability of such transgenic animals makes possible new approaches to the production of fully human antibodies. Antibodies with various immunospecificities are desirable for therapeutic and diagnostic use. Those antibodies intended for human therapeutic and in vivo diagnostic use, in particular, have been problematic because prior art sources for such antibodies resulted in immunoglobulins bearing the characteristic structures of antibodies produced by nonhuman hosts. Such antibodies tend to be immunogenic when used in humans.

The availability of the nonhuman, immunogen-responsive transgenic animals described in the above-referenced WO 94/02602 makes possible convenient production of human antibodies without the necessity of employing human hosts.

DISCLOSURE OF THE INVENTION

The invention is directed to methods to produce human antibodies by a process wherein at least one step of the process includes immunizing a transgenic nonhuman animal with the desired antigen. The modified animal fails to produce endogenous antibodies, but instead produces B-cells which secrete immunoglobulins with fully human variable regions. The antibodies produced include fully human antibodies and can be obtained from the animal directly, or from immortalized B-cells derived from the animal. Alternatively, the genes encoding the immunoglobulins with human variable regions can be recovered and expressed to obtain the antibodies directly or modified to obtain analogs of antibodies such as, for example, single chain $F_V$ molecules.

Thus, in one aspect, the invention is directed to a method to produce an immunoglobulin with a fully human variable region to a specific antigen or to produce an analog of said immunoglobulin by a process which comprises immunizing a nonhuman animal with the antigen under conditions that stimulate an immune response. The nonhuman animal is characterized by being substantially incapable of producing endogenous heavy or light immunoglobulin chain, but capable of producing immunoglobulins either with both human variable regions and constant regions or with fully human variable regions or both. In the resulting immune response, the animal produces B cells which secrete immunoglobulins, with at least variable regions that are fully human, specific for the antigen. The human immunoglobulin of desired specificity can be directly recovered from the animal, for example, from the serum, or primary B cells can be obtained from the animal and immortalized. The immortalized B cells can be used directly as the source of human antibodies or, alternatively, the genes encoding the antibodies can be prepared from the immortalized B cells or from primary B cells of the blood or lymphoid tissue (spleen, tonsils, lymph nodes, bone marrow) of the immunized animal and expressed in recombinant hosts, with or without modification, to produce the immunoglobulin or its analogs. In addition, the genes encoding the repertoire of immunoglobulins produced by the immunized animal can be used to generate a library of immunoglobulins to permit screening for those variable regions which provide the desired affinity. Clones from the library which have the desired characteristics can then be used as a source of nucleotide sequences encoding the desired variable regions for further manipulation to generate antibodies or analogs with these characteristics using standard recombinant techniques.

In another aspect, the invention relates to an immortalized nonhuman B cell line derived from the above described animal. In still another aspect, the invention is directed to a recombinant host cell which is modified to contain the gene encoding either the human immunoglobulin with the desired specificity, or an analog thereof which exhibits the same specificity.

In still other aspects, the invention is directed to antibodies or antibody analogs prepared by the above described methods and to recombinant materials for their production.

In still other aspects, the invention is directed to antibodies with fully human variable regions, including fully human antibodies which are immunospecific with respect to particular antigens set forth herein and to analogs which are similarly immunospecific, as well as to the recombinant materials useful in the production of these antibodies.

BRIEF DESCRIPTION OF THE DRAWINGS

FIG. 19 shows the complete nucleotide sequence of the light chain from the antibody secreted by D5.1 (SEQ ID NOS 18–22).

MODES OF CARRYING OUT THE INVENTION

Figure 1:
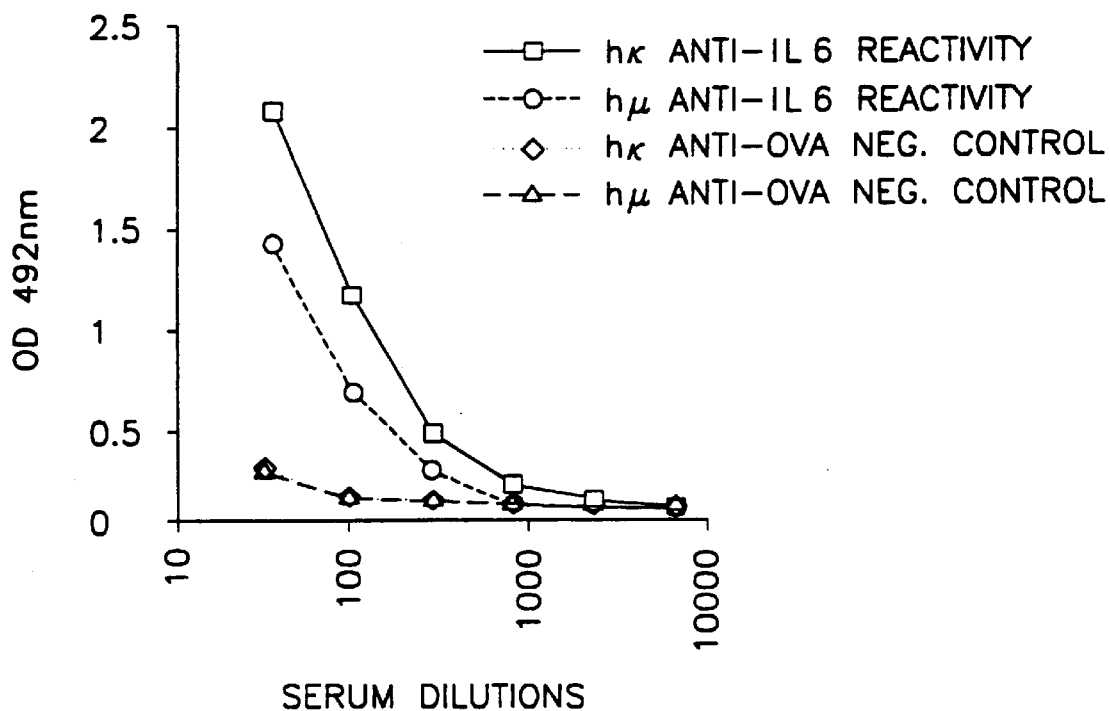
FIG. 1 shows the serum titers of anti-IL-6 antibodies from a xenomouse immunized with human IL-6 and which antibodies contain human kappa light chains and/or human $\mu$ heavy chains.

In general, the methods of the invention include administering an antigen for which human forms of immunospecific reagents are desired to a transgenic nonhuman animal which has been modified genetically so as to be capable of producing human, but not endogenous, antibodies. Typically, the animal has been modified to disable the endogenous heavy and/or light chain loci in its genome, so that these endogenous loci are incapable of the rearrangement required to generate genes encoding immunoglobulins in response to an antigen. In addition, the animal will have been provided, stably, in its genome, at least one human heavy chain locus and at least one human light chain locus so that in response to an administered antigen, the human loci can rearrange to provide genes encoding human immunoglobulins immunospecific for the antigen.

The details for constructing such an animal useful in the method of the invention are provided in the PCT application WO 94/02602 referenced above.

For production of the desired antibodies, the first step is administration of the antigen. Techniques for such administration are conventional and involve suitable immunization protocols and formulations which will depend on the nature of the antigen per se. It may be necessary to provide the antigen with a carrier to enhance its immunogenicity and/or to include formulations which contain adjuvants and/or to administer multiple injections, and the like. Such techniques are standard and optimization of them will depend on the characteristics of the particular antigen for which immunospecific reagents are desired.

As used herein, the term "immunospecific reagents" includes immunoglobulins and their analogs. The term "analogs" has a specific meaning in this context. It refers to moieties that contain the fully human portions of the immunoglobulin which account for its immunospecificity. In particular, variable regions including the complementarity determining regions (CDRs) are required, along with sufficient portions of the framework regions (FRs) to result in the appropriate three dimensional conformation. Typical immunospecific analogs of antibodies include $F_{(ab')_2}$, $F_{ab'}$, and $F_{ab}$ regions. Modified forms of the variable regions to obtain, for example, single chain $F_V$ analogs with the appropriate immunospecificity are known. A review of such $F_V$ construction is found, for example, in Tibtech (1991) 9: . The construction of antibody analogs with multiple immunospecificities is also possible by coupling the human variable regions derived from antibodies with varying specificities.

The variable regions with fully human characteristics can also be coupled to a variety of additional substances which can provide toxicity, biological functionality, alternative binding specificities and the like. The moieties including the fully human variable regions produced by the methods of the invention include single-chain fusion proteins, molecules coupled by covalent methods other than those involving peptide linkages, and aggregated molecules. Examples of analogs which include variable regions coupled to additional molecules covalently or noncovalently include those in the following nonlimiting illustrative list. Traunecker, A. et al. *Int J Cancer Supp* (1992) *Supp* 7:51–describe the bispecific reagent janusin in which the $F_V$ region directed to CD3 is coupled to soluble CD4 or to other ligands such as OVCA and IL-7. Similarly, the fully human variable regions produced by the method of the invention can be constructed into $F_V$ molecules and coupled to alternative ligands such as those illustrated in the cited article. Higgins, P. J. et al. *J Infect Disease* (1992) 166:198–202 describe a heteroconjugate antibody composed of OKT3 cross-linked to an antibody directed to a specific sequence in the V3 region or GP120. Such heteroconjugate antibodies can also be constructed using at least the human variable regions contained in the immunoglobulins produced by the invention methods. Additional examples of bispecific antibodies include those described by Fanger, M. W. et al. *Cancer Treat Res* (1993) 68:181–194 and by Fanger, M. W. et al. *Crit Rev Immunol* (1992) 12:101–124. Conjugates that are immunotoxins including conventional antibodies have been widely described in the art. The toxins may be coupled to the antibodies by conventional coupling techniques or immunotoxins containing protein toxin portions can be produced as fusion proteins. The analogs of the present invention can be used in a corresponding way to obtain such immunotoxins. Illustrative of such immunotoxins are those described by Byrs, B. S. et al. *Seminars Cell Biol* (1991) 2:59–70 and by Fanger, M. W. et al. *Immunol Today* (1991) 12:51–54.

In short, the genes encoding the immunoglobulins produced by the transgenic animals of the invention can be retrieved and the nucleotide sequences encoding the fully human variable region can be manipulated according to known techniques to provide a variety of analogs such as those described above. In addition, the immunoglobulins themselves containing the human variable regions can be modified using standard coupling techniques to provide conjugates retaining immunospecificity and fully human characteristics in the immunospecific region.

Thus, immunoglobulin "analogs" refers to moieties which contain those portions of the antibodies of the invention which retain their human characteristics and their immunospecificity. These will retain sufficient human variable region to provide the desired specificity.

As stated above, all of the methods of the invention include administering the appropriate antigen to the transgenic animal. The recovery or production of the antibodies themselves can be achieved in various ways.

First, and most straightforward, the polyclonal antibodies produced by the animal and secreted into the bloodstream can be recovered using known techniques. Purified forms of these antibodies can, of course, be readily prepared by standard purification techniques, preferably including affinity chromatography with respect to the particular antigen, or even with respect to the particular epitope of the antigen for which specificity is desired. In any case, in order to monitor the success of immunization, the antibody levels with respect to the antigen in serum will be monitored using standard techniques such as ELISA, RIA and the like.

It will be noted, from the examples below, that a portion of the polyclonal antiserum obtained may include an endogenous heavy chain constant region derived from the host, even though the variable regions are fully human. Under these circumstances, to the extent that an application requires fully human antibodies, use of the polyclonal antiserum directly would be inappropriate. However, the presence of these chimeras, which is believed to result from in vivo isotype switching as described by Gerstein et al. *Cell* (1990) 63:537, is not problematic, in view of conventional purification and modification methods and in view of the availability of alternative methods to recover fully human antibodies, if desired, described in the following paragraphs.

First, and most simply, the polyclonal antiserum could be subjected to suitable separation techniques to provide compositions containing only fully human immunoglobulins. Portions of the serum which display characteristics of the host species can be removed, for example, using affinity reagents with the appropriate anti species immunoglobulins or immunospecific portions thereof. Furthermore, for applications where only the variable regions of the antibodies are required, treating the polyclonal antiserum with suitable reagents so as to generate $F_{ab}$, $F_{ab'}$, or $F_{(ab')_2}$ portions results in compositions containing fully human characteristics. Such fragments are sufficient for use, for example, in immunodiagnostic procedures involving coupling the immunospecific portions of immunoglobulins to detecting reagents such as radioisotopes. Thus, for some applications, the polyclonal antiserum can be treated to provide compositions with the desired characteristics including compositions consisting essentially of fully human antibodies and compositions including immunoglobulin analogs wherein the immunospecific portion is fully human.

Alternatively, immunoglobulins and analogs with desired characteristics can be generated from immortalized B cells derived from the transgenic animals used in the method of the invention or from the rearranged genes provided by these animals in response to immunization. It will be apparent that hybridomas derived from the B cells of the immunized animal can be screened so as to choose only those secreting fully human antibodies and that the genetic material can be recovered from the hybridomas or from lymphocytes in spleen, blood, or lymph nodes of the immunized animal and manipulated using conventional techniques to replace any endogenous constant region with a human one or to produce a desired analog.

Thus, as an alternative to harvesting the antibodies directly from the animal, the B cells can be obtained, typically from the spleen, but also, if desired, from the peripheral blood lymphocytes or lymph nodes and immortalized using any of a variety of techniques, most commonly using the fusion methods described by Kohler and Milstein. The resulting hybridomas (or otherwise immortalized B cells) can then be cultured as single colonies and screened for secretion of antibodies of the desired specificity. As described above, the screen can also include a determination of the fully human character of the antibody. For example, as described in the examples below, a sandwich ELISA wherein the monoclonal in the hybridoma supernatant is bound both to antigen and to an antihuman constant region can be employed. Conversely, hybridomas that secrete antibodies which are immunoreactive with antispecies antibodies directed to the species of the immunized animal can be discarded. After the appropriate hybridomas are selected, the desired antibodies can be recovered, again using conventional techniques. They can be prepared in quantity by culturing the immortalized B cells using conventional methods, either in vitro, or in vivo to produce ascites fluid. Purification of the resulting monoclonal antibody preparations is less burdensome than in the case of serum since each immortalized colony will secrete only a single type of antibody. In any event, standard purification techniques to isolate the antibody from other proteins in the culture medium can be employed.

As an alternative to obtaining human immunoglobulins directly from the culture of immortalized B cells derived from the animal, the immortalized cells can be used as a source of rearranged heavy chain and light chain loci for subsequent expression and/or genetic manipulation. Isolation of genes from such antibody-producing cells is straightforward since high levels of the appropriate mRNAs are available for production of a cDNA library. The recovered rearranged loci can be manipulated as desired. For example, the constant region can be exchanged for that of a different isotype or that of a human antibody, as described above, or eliminated altogether. The variable regions can be linked to encode single chain $F_V$ regions. Multiple $F_V$ regions can be linked to confer binding ability to more than one target or chimeric heavy and light chain combinations can be employed. Once the genetic material is available, design of analogs as described above which retain their ability to bind the desired target, as well as their human characteristics, is straightforward.

Once the appropriate genetic material is obtained and, if desired, modified to encode an analog, the coding sequences including those that encode, at a minimum, the variable regions of the human heavy and light chain can be inserted into expression systems contained on vectors which can be transfected into standard recombinant host cells. As described below, a variety of such host cells may be used; for efficient processing, however, mammalian cells are preferred. Typical mammalian cell lines useful for this purpose include CHO cells, 293 cells, or NSO-GS cells.

The production of the antibody or analog is then undertaken by culturing the modified recombinant host under culture conditions appropriate for the growth of the host cells and the expression of the coding sequences. The antibodies are then recovered from the culture. The expression systems are preferably designed to include signal peptides so that the resulting antibodies are secreted into the medium; however, intracellular production is also possible.

In addition to deliberate design of modified forms of the immunoglobulin genes to produce analogs, advantage can be taken of phage display techniques to provide libraries containing a repertoire of antibodies with varying affinities for the desired antigen. For production of such repertoires, it is unnecessary to immortalize the B cells from the immunized animal; rather the primary B cells can be used directly as a source of DNA. The mixture of cDNAs obtained from B cells, e.g., derived from spleens, is used to prepare an expression library, for example, a phage display library transfected into *E. coli*. The resulting cells are tested for immunoreactivity to the desired antigen. Techniques for the identification of high affinity human antibodies from such libraries are described by Griffiths, A. D., et al., *EMBO J* (1994) 13:3245–3260; by Nissim, A., et al. *ibid,* 692–698, and by Griffiths, A. D., et al., *ibid,* 725–734. Ultimately, clones from the library are identified which produce binding affinities of a desired magnitude for the antigen, and the DNA encoding the product responsible for such binding is recovered and manipulated for standard recombinant expression. Phage display libraries may also be constructed using previously manipulated nucleotide sequences and screened in similar fashion. In general, the cDNAs encoding heavy and light chain are independently supplied or are linked to form $F_V$ analogs for production in the phage library.

The phage library is thus screened for the antibodies with highest affinity for the antigen and the genetic material recovered from the appropriate clone. Further rounds of screening can increase the affinity of the original antibody isolated. The manipulations described above for recombinant production of the antibody or modification to form a desired analog can then be employed.

As above, the modified or unmodified rearranged loci are manipulated using standard recombinant techniques by constructing expression systems operable in a desired host cell, such as, typically, a Chinese hamster ovary cell, and the desired immunoglobulin or analog is produced using standard recombinant expression techniques, and recovered and purified using conventional methods.

The application of the foregoing processes to antibody production has enabled the preparation of human immunospecific reagents with respect to antigens for which human antibodies have not heretofore been available. The immunoglobulins that result from the above-described methods and the analogs made possible thereby, provide novel compositions for use in analysis, diagnosis, research, and therapy. The particular use will, of course, depend on the immunoglobulin or analog prepared. In general, the compositions of the invention will have utilities similar to those ascribable to nonhuman antibodies directed against the same antigen. Such utilities include, for example, use as a affinity ligands for purification, as reagents in immunoassays, as components of immunoconjugates, and as therapeutic agents for appropriate indications.

Particularly in the case of therapeutic agents or diagnostic agents for use in vivo, it is highly advantageous to employ antibodies or their analogs with fully human characteristics. These reagents avoid the undesired immune responses engendered by antibodies or analogs which have characteristics marking them as originating from non-human species. Other attempts to "humanize" antibodies do not result in reagents with fully human characteristics. For example, chimeric antibodies with murine variable regions and human constant regions are easily prepared, but, of course, retain murine characteristics in the variable regions. Even the much more difficult procedure of "humanizing" the variable regions by manipulating the genes encoding the amino acid sequences that form the framework regions does not provide the desired result since the CDRs, typically of nonhuman origin, cannot be manipulated without destroying immunospecificity. Thus, the methods of the present invention provide, for the first time, immunoglobulins that are fully human or analogs which contain immunospecific regions with fully human characteristics.

There are large numbers of antigens for which human antibodies and their human analogs would be made available by the methods of the invention. These include the following as a nonlimiting set:

leukocyte markers, such as CD2, CD3, CD4, CD5, CD6, CD7, CD8, CD11a,b,c, CD13, CD14, CD18, CD19, CD20, CD22, CD23, CD27 and its ligand, CD28 and its ligands B7.1, B7.2, B7.3, CD29 and its ligand, CD30 and its ligand, CD40 and its ligand gp39, CD44, CD45 and isoforms, CDw52 (Campath antigen), CD56, CD58, CD69, CD72, CTLA-4, LFA-1 and TCR histocompatibility antigens, such as MHC class I or II, the Lewis Y antigens, SLex, SLey, SLea, and SLeb;

integrins, such as VLA-1, VLA-2, VLA-3, VLA-4, VLA-5, VLA-6, and LFA-1;

adhesion molecules, such as Mac-1 and p150,95;

selectins, such as L-selectin, P-selectin, and E-selectin and their counterreceptors VCAM-1, ICAM-1, ICAM-2, and LFA-3;

interleukins, such as IL-1, IL-2, IL-3, IL-4, IL-5, IL-6, IL-7, IL-8, IL-10, IL-11, IL-12, IL-13, IL-14, and IL-15;

interleukin receptors, such as IL-1R, IL-2R, IL-4R, IL-5R, IL-6R, IL-7R, IL-8R, IL-10R, IL-11R, IL-12R, IL-13R, IL-14R, and IL-15R;

chemokines, such as PF4, RANTES, MIP1α, MCP1, NAP-2, Groα, Groβ, and IL-8;

growth factors, such as TNFalpha, TGFbeta, TSH, VEGF/VPF, PTHrP, EGF family, FGF, PDGF family, endothelin, and gastrin releasing peptide (GRP);

growth factor receptors, such as TNFalphaR, RGFbetaR, TSHR, VEGFR/VPFR, FGFR, EGFR, PTHrPR, PDGFR family, EPO-R, GCSF-R and other hematopoietic receptors;

interferon receptors, such as IFNαR, IFNβR, and IFNγR;

Igs and their receptors, such as IgE, FceRI, and FCeRII;

tumor antigens, such as her2-neu, mucin, CEA and endosialin;

allergens, such as house dust mite antigen, lol p1 (grass) antigens, and urushiol;

viral proteins, such as CMV glycoproteins B, H, and gCIII, HIV-1 envelope glycoproteins, RSV envelope glycoproteins, HSV envelope glycoproteins, EBV envelope glycoproteins, VZV envelope glycoproteins, HPV envelope glycoproteins, Hepatitis family surface antigens;

toxins, such as pseudomonas endotoxin and osteopontin/uropontin, snake venom, and bee venom;

blood factors, such as complement C3b, complement C5a, complement C5b-9, Rh factor, fibrinogen, fibrin, and myelin associated growth inhibitor;

enzymes, such as cholesterol ester transfer protein, membrane bound matrix metalloproteases, and glutamic acid decarboxylase (GAD); and miscellaneous antigens including ganglioside GD3, ganglioside GM2, LMP1, LMP2, eosinophil major basic protein, eosinophil cationic protein, PANCA, Amadori protein, Type IV collagen, glycated lipids, γ-interferon, A7, P-glycoprotein and Fas (AFO-1) and oxidized-LDL.

Particularly preferred immunoglobulins and analogs are those immunospecific with respect to human IL-6, human IL-8, human TNFα, human CD4, human L-selectin, and human gp39. Human antibodies against IL-8 are particularly useful in preventing tumor metastasis and inflammatory states such as asthma. Antibodies and analogs immunoreactive with human TNFα and human IL-6 are useful in treating cachexia and septic shock as well as autoimmune disease. Antibodies and analogs immunoreactive with gp39 or with L-selectin are also effective in treating or preventing autoimmune disease. In addition, anti-gp39 is helpful in treating graft versus host disease, in preventing organ transplant rejection, and in treating glomerulonephritis. Antibodies and analogs against L-selectin are useful in treating ischemia associated with reperfusion injury.

Typical autoimmune diseases which can be treated using the above-mentioned antibodies and analogs include systemic lupus erythematosus, rheumatoid arthritis, psoriasis, Sjogren's, scleroderma, mixed connective tissue disease, dermatomyositis, polymyositis, Reiter's syndrome, Behcet's disease, Type 1 diabetes, Hashimoto's thyroiditis, Grave's disease, multiple sclerosis, myasthenia gravis and pemphigus.

The examples below are intended to illustrate but not to limit the invention.

In these examples, mice, designated "xenomice", are used for initial immunizations. A detailed description of such xenomice is found in the above-referenced PCT application WO 94/02602. Immunization protocols appropriate to each antigen are described in the specific examples below. The sera of the immunized xenomice (or the supernatants from immortalized B cells) were titrated for antigen specific human antibodies in each case using a standard ELISA format. In this format, the antigen used for immunization was immobilized onto wells of microtiter plates. The plates were washed and blocked and the sera (or supernatants) were added as serial dilutions for 1–2 hours of incubation. After washing, bound antibody having human characteristics was detected by adding the appropriate antispecies Ig (typically antihuman kappa or antihuman μ) conjugated to horseradish peroxidase (HRP) for one hour. In some cases, the bound antibodies were tested for murine characteristics using antimurine antibodies, typically antimurine γ. After again washing, the chromogenic reagent o-phenylene diamine (OPD) substrate and hydrogen peroxide were added and the plates were read 30 minutes later at 492 nm using a microplate reader.

Unless otherwise noted, the antigen was coated using plate coating buffer (0.1 M carbonate buffer, pH 9.6); the assay blocking buffer used was 0.5% BSA, 0.1% Tween 20 and 0.0% Thimerosal in PBS; the substrate buffer used in color development was citric acid 7.14 g/l: dibasic sodium phosphate 17.96 g/l; the developing solution (made immediately before use) was 10 ml substrate buffer, 10 mg OPD, plus 5 ml hydrogen peroxide; the stop solution (used to stop color development) was 2 M sulfuric acid. The wash solution was 0.05% Tween 20 in PBS.

EXAMPLE 1

Human Antibodies Against Human IL-6

Three to 5 xenomice aged 8–20 weeks were age-matched and immunized intraperitoneally with 50 μg human IL-6 emulsified in complete Freund's adjuvant for primary immunization and in incomplete Freund's adjuvant for subsequent injections. The mice received 6 injections 2–3 weeks apart. Serum titers were determined after the second dose and following each dose thereafter. Bleeds were performed 6–7 days after injections from the retrobulbar plexus. The blood was allowed to clot at room temperature for about 2 hours and then incubated at 4° C. for at least 2 hours before separating and collecting the sera.

ELISAs were conducted as described above by applying 100 μl per well of recombinant human IL-6 at 2 mg/ml in coating buffer. Plates were then incubated at 4° C. overnight or at 37° C. for 2 hours and then washed three times in washing buffer. Addition of 100 μl/well blocking buffer was followed by incubation at room temperature for 2 hours, and an additional 3 washes.

Then, 50 μl/well of diluted serum samples (and positive and negative controls) were added to the plates. Plates were then incubated at room temperature for 2 hours and again washed 3 times.

After washing, 100 μl per well of either HRP-mouse antihuman IgM at 1/2,000 or HRP-mouse antihuman kappa at 1/2,000, diluted in blocking buffer were added. After a 1 hour incubation at room temperature, the plates were washed 3 times and developed with OPD substrate for 10–25 minutes. 50 μl/well of stop solution were then added and the results read on an ELISA plate reader at 492 nm. The dilution curves resulting from the titration of serum from xenomouse A40-7 after 6 injections are shown in FIG. 1. The data in FIG. 1 show production of anti-IL-6 immunoreactive with antihuman kappa and antihuman μ detectable at serum dilutions above 1:1,000.

EXAMPLE 2
Human Antibodies Against Human IL-8

Immunization and serum preparation were as described in Example 1 as except that human recombinant IL-8 was used as an immunogen.

Figure 2:
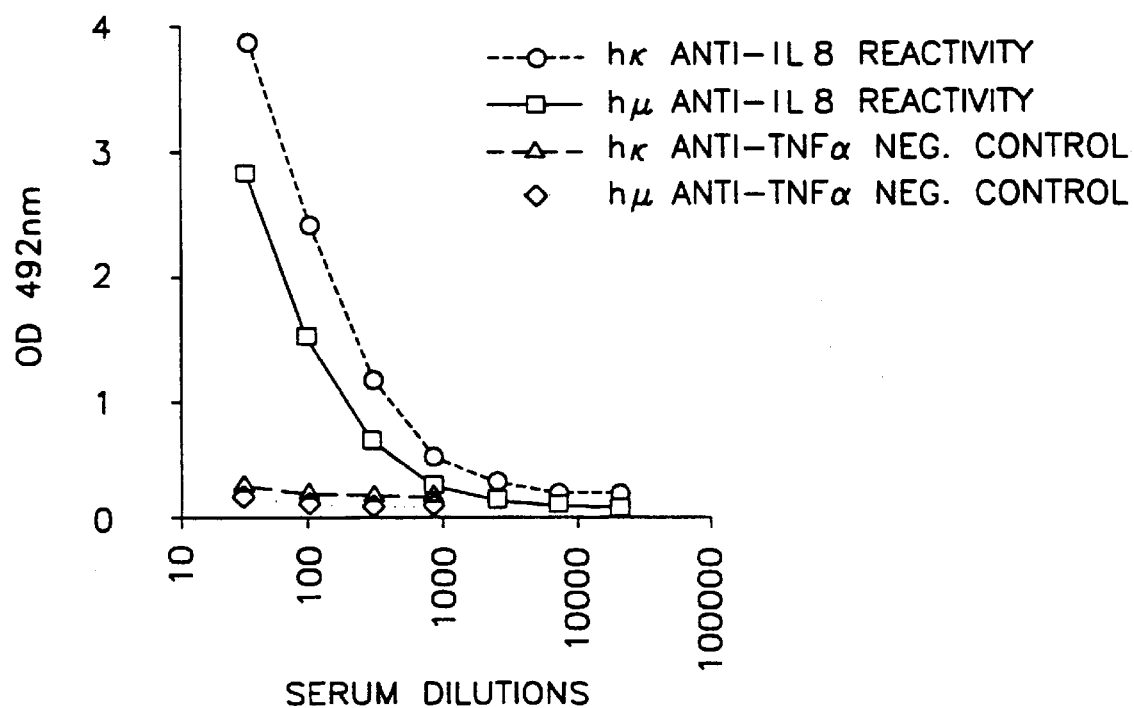
FIG. 2 shows the serum titers of anti-IL-8 antibodies from a xenomouse immunized with human IL-8 and which antibodies contain human kappa light chains and/or human $\mu$ heavy chains.

ELISA assays were performed with respect to the recovered serum, also exactly as described in Example 1, except that the ELISA plates were initially coated using 100 μl/well of recombinant human IL-8 at 0.5 mg/ml in the coating buffer. The results obtained for various serum dilutions from xenomouse A260-5 after 6 injections are shown in FIG. 2. Human anti-IL-8 reactivity was again shown at serum dilutions having concentrations higher than that represented by a 1:1,000 dilution.

EXAMPLE 3
Human Antibodies Against Human TNFα

Immunization and serum preparation were conducted as described in Example 1 except that human recombinant TNFα was substituted for human IL-6. ELISAs were conducted as described in Example 1 except that the initial coating of the ELISA plate employed 100 μl/well recombinant human TNFα at 1 mg/ml in coating buffer.

Figure 3:
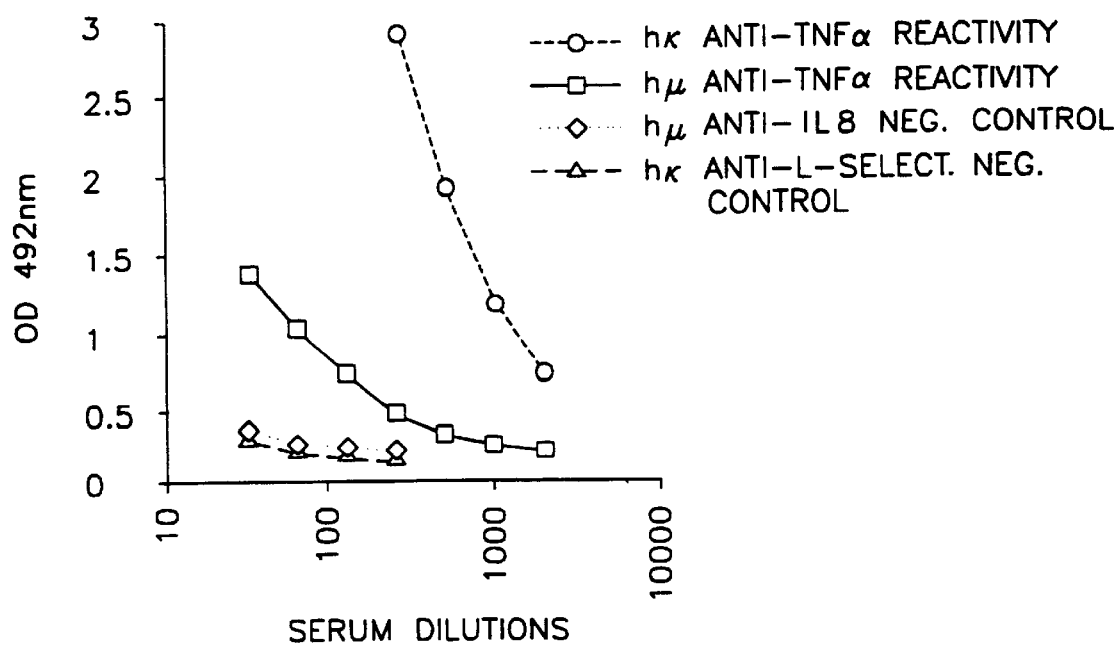
FIG. 3 shows the serum titers of anti-TNFα antibodies from a xenomouse immunized with human TNF-α and which antibodies contain human kappa light chains and/or human α heavy chains.

The dilution curves for serum from xenomouse A210-8 after 6 injections obtained are shown in FIG. 3. Again significant titers of human anti-TNFα reactivity were shown.

EXAMPLE 4
Human Antibodies Against Human CD4

The human CD4 antigen was prepared as a surface protein on transfected recombinant cells as follows: Human CD4 zeta (F15 LTR) as described in Roberts, et al., *Blood* (1994) 84:2878 was introduced into the rat basophil leukemic cell line RBL-2H3, described by Callan, M., et al., *Proc Natl Acad Sci USA* (1993) 90:10454 using the kat high efficiency transduction system described by Finer, et al., *Blood* (1994) 83:43. Briefly, RBL-2H3 cells at $10^6$ cells per well were cultured in 750 ml DMEM$^{low}$+20% FBS (Gibco) and 16 μg/ml polybrene with an equal volume of proviral supernatant for 2 hours at 37° C., 5% $CO_2$. One ml of medium was removed and 750 μl of infection medium and retroviral supernatant were added to each well and the cultures incubated overnight. The cells were washed and expanded in DMEM$^{low}$+10% FBS until sufficient cells were available for sorting. The CD4-zeta transduced RBL-2H3 cells were sorted using the FACSTAR plus (Becton Dickinson). The cells were stained for human CD4 with a mouse antihuman CD4-PE antibody and the top 2–3% expressing cells were selected.

Figure 4:
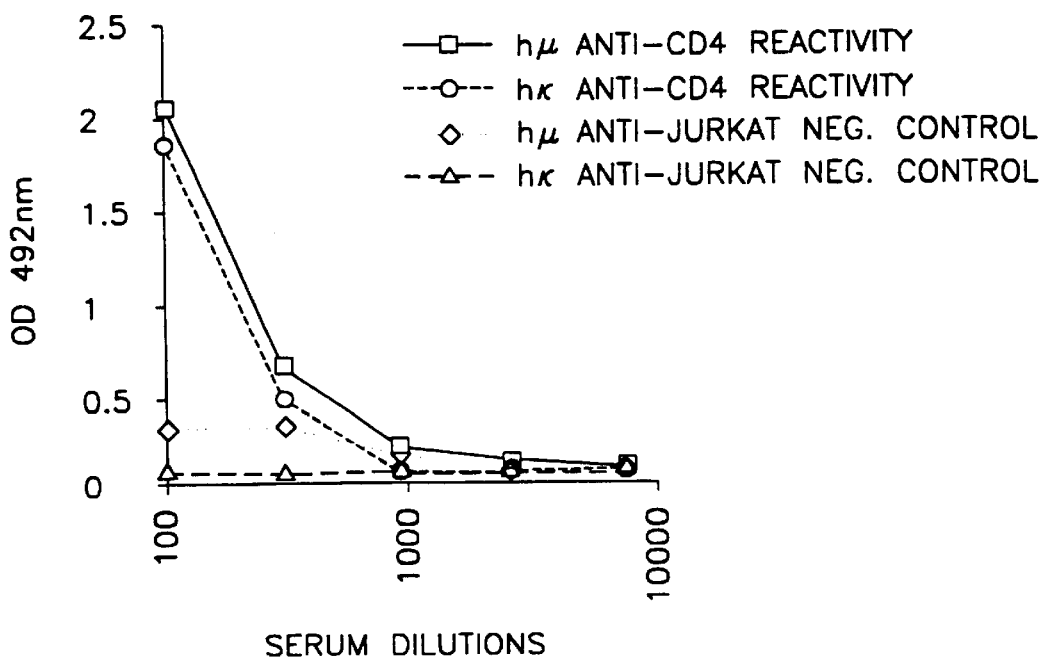
FIG. 4 shows the serum titers of anti-CD4 antibodies from a xenomouse immunized with human CD4 and which antibodies contain human kappa light chains and/or human α heavy chains.

Immunizations were conducted as described in Example 1 using $10 \times 10^6$ cells per mouse except that the primary injection was subcutaneous at the base of the neck. The mice received 6 injections 2–3 weeks apart. Serum was prepared and analyzed by ELISA as described in Example 1 except that the initial coating of the ELISA plate utilized 100 μl per well of recombinant soluble CD4 at 2 mg/ml of coating buffer. The titration curve for serum from xenomouse A207-1 after 6 injections is shown in FIG. 4. Titers of human anti-CD4 reactivity were shown at concentrations representing greater than those at 1:1,000 dilution.

EXAMPLE 5
Human Antibodies Against Human L-selectin

The antigen was prepared as a surface displayed protein in C51 cells, a high expressing clone derived by transfecting the mouse pre-B cell 300.19 with LAM-1 cDNA (LAM-1 is the gene encoding L-selectin) (Tedder, et al., *J Immunol* (1990) 144:532) or with similarly transfected CHO cells. The transfected cells were sorted using fluorescent activated cell sorting using anti-Leu-8 antibody as label.

The C51 and the transfected CHO cells were grown in DME 4.5 g/l glucose with 10% FCS and 1 mg/ml G418 in 100 mm dishes. Negative control cells, 3T3-P317 (transfected with gag/pol/env genes of Moloney virus) were grown in the same medium without G418.

Primary immunization was by injection subcutaneously at the base of the neck; subsequent injections were intraperitoneal. 70–100 million C51 or transfected CHO cells were used per injection for a total of five injections 2–3 weeks apart.

Sera were collected as described in Example 1 and analyzed by ELISA in a protocol similar to that set forth in Example 1.

For the ELISA, the transfected cells were plated into 96 well plates and cell monolayers grown for 1–2 days depending on cell number and used for ELISA when confluent. The cells were fixed by first washing with cold 1×PBS and then fixing solution (5% glacial acetic acid, 95% ethanol) was added. The plates were incubated at −25° C. for 5 minutes and can be stored at this temperature if sealed with plate sealers.

The ELISA is begun by bringing the plates to room temperature, flicking to remove fixing solution and washing 5 times with DMEM medium containing 10% FCS at 200 μl per well.

The wells were treated with various serum dilutions or with positive or negative controls. Positive control wells contained murine IgG1 to human L-selectin.

Figure 5:
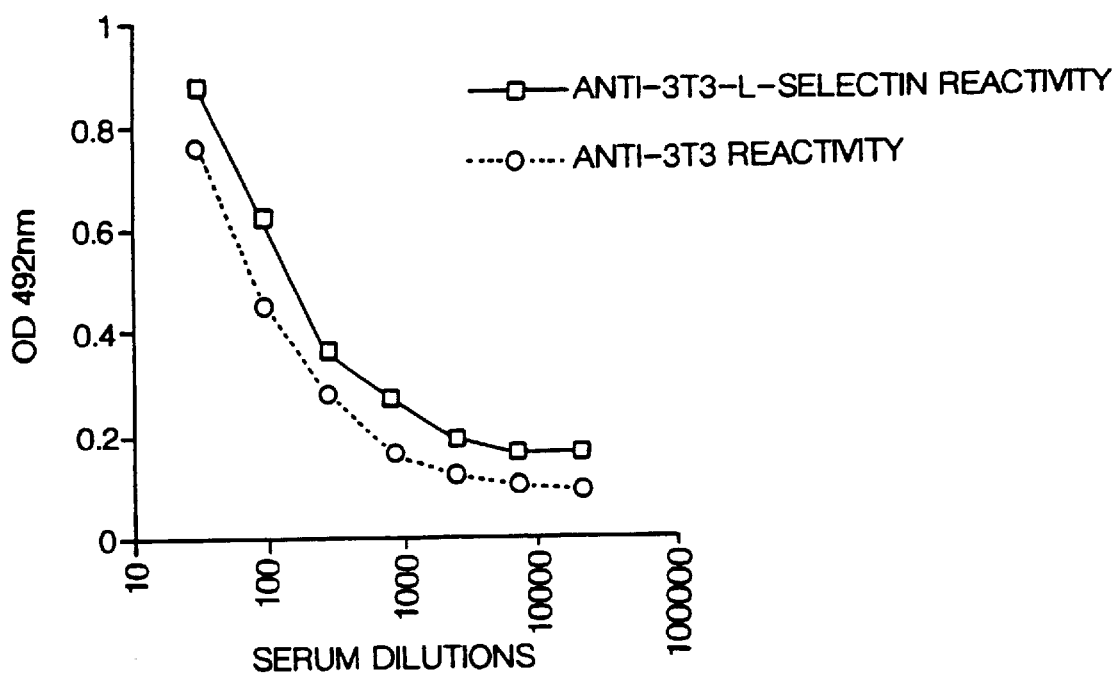
FIG. 5 shows the serum titers of a xenomouse immunized with 300.19 cells expressing L-selectin at their surface. In the ELISA assay used, these antibodies are detectable only if they carry human $\mu$ constant region heavy chains.
Figure 6:
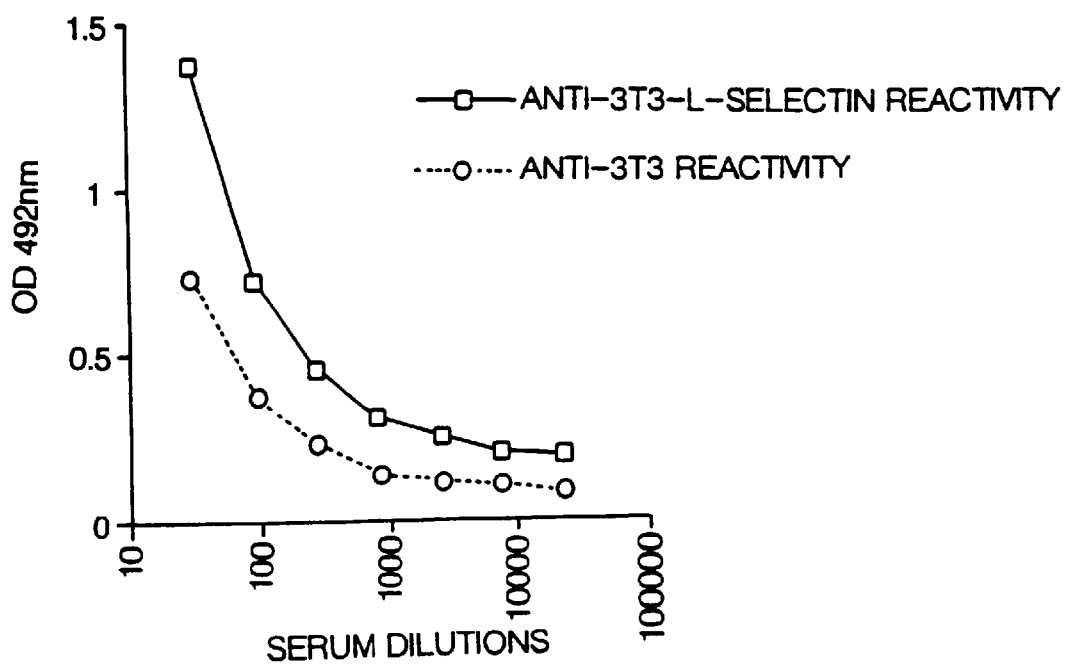
FIG. 6 shows the serum titers of a xenomouse immunized with 300.19 cells expressing L-selectin at their surface. In the ELISA assay used, these antibodies are detectable only if they carry human kappa light chains.

The wells were incubated for 45 minutes and monolayer integrity was checked under a microscope. The wells were then incubated with either HRP-antimouse IgG (1/1000) or with the antihuman kappa or antihuman μ conjugates described in Example 1. The plates were then washed with 1% BSA/PBS and again with PBS and monolayer integrity was checked. The plates were developed, stopped, and read as described above. The results for serum from xenomouse A303-3 are shown in FIGS. 5 and 6; human antibodies both to L-selectin and control 3T3 cells were obtained. However, the serum titers are higher for the L-selectin-expressing cells as compared to parental 3T3 cells. These results show that xenomouse A303-3 produces antibodies specific for L-selectin with human μ heavy chain regions and/or human kappa light chains.

ELISAs were also performed using as the immobilized antigen a fusion protein consisting of the extracellular domain of human L-selectin fused to the constant domain of human $IgG_1$ (Guo, et al., *Cell Immunol* (1994) 154:202). The L-selectin fusion protein was made by transient transfection of human 293 cells using calcium phosphate transfection (Wigler, M., *Cell* (1979) 16:777). Serum preparation was performed as described in Example 1. ELISAs were conducted essentially as in Example 1, except that the initial coating of the ELISA plate employed 100 μl transfected 293 cell culture supernatant containing the L-selectin-Ig fusion protein. Detection employed HRP-mouse antihuman kappa and HRP-goat antimouse IgG.

Figure 7:
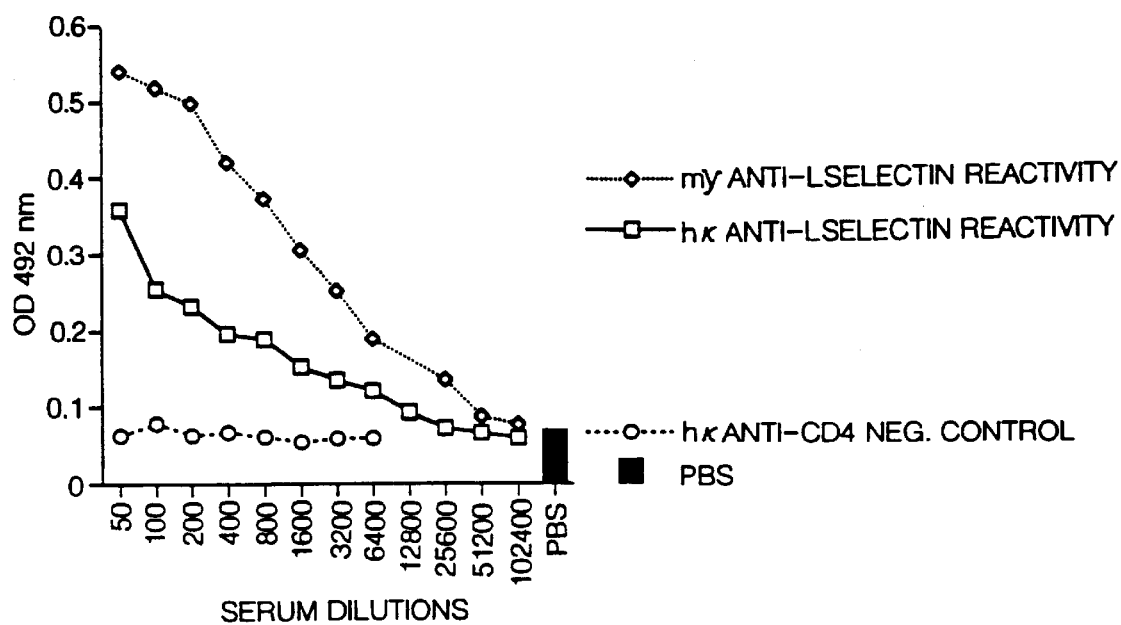
FIG. 7 shows the serum titers of a xenomouse immunized with 300.19 cells expressing L-selectin. In this ELISA, these antibodies are detectable if they carry human kappa light chain and/or murine γ constant regions.

FIG. 7 shows the results from xenomouse A195-2; antibodies specific for L-selectin having human kappa light chains and/or murine heavy chain γ regions are present in the serum.

The antisera obtained from the immunized xenomice were also tested for staining of human neutrophils. Human neutrophils were prepared as follows: peripheral blood was collected from normal volunteers with 100 units/ml heparin.

About 3.5 ml blood was layered over an equal volume of One-step Polymorph Gradient (Accurate Chemical, Westbury, N.Y.) and spun for 30 minutes at 450×G at 20° C. The neutrophil fraction was removed and washed twice in DPBS/2% FBS.

The neutrophils were then stained with either:

(1) antiserum from xenomouse A195-2 immunized with C51 cells (expressing L-selectin);

(2) as a positive control, mouse monoclonal antibody LAM1-3 (against L-selectin); and (3) as negative control, antiserum from a xenomouse immunized with cells expressing human gp39.

Figure 8:
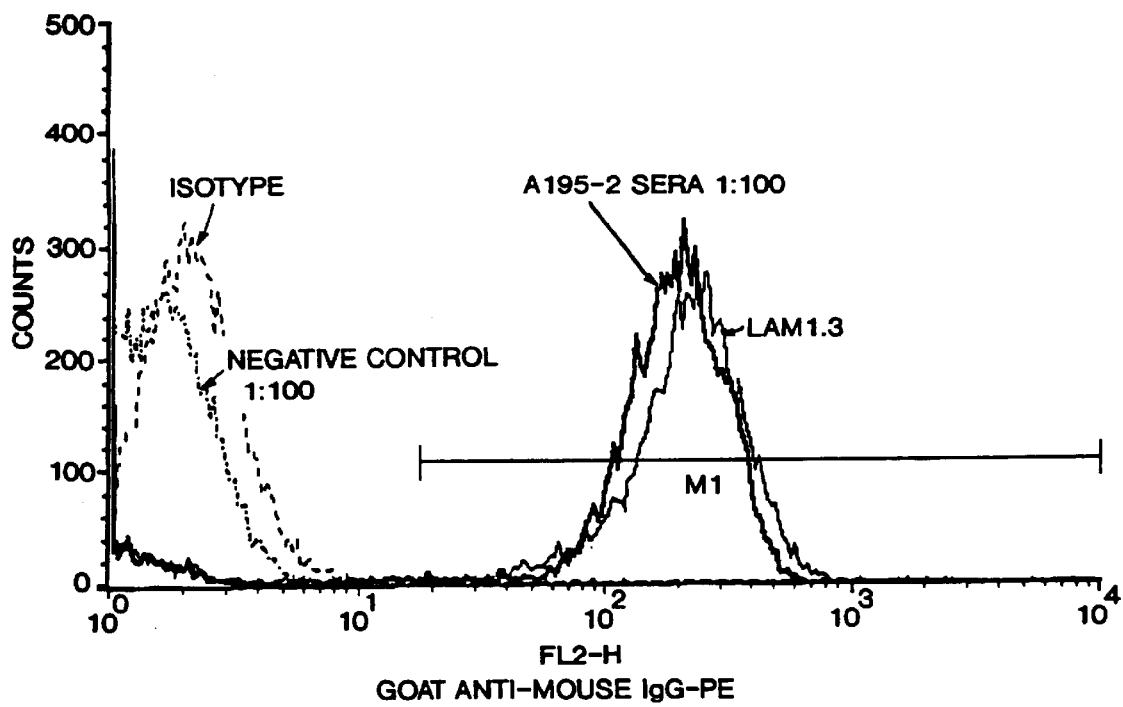
FIG. 8 shows a FACS analysis of human neutrophils coupled to sera from a xenomouse (A195-2) immunized with human L-selectin and labeled with an antibody immunoreactive with murine heavy chain γ constant region.
Figure 9:
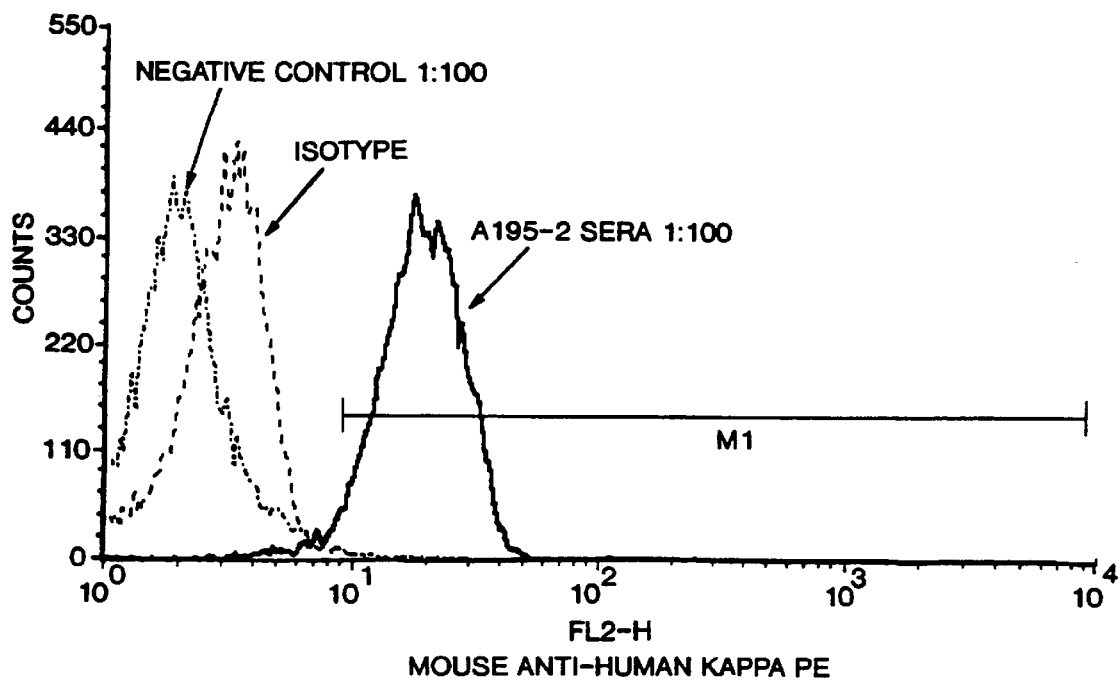
FIG. 9 shows a FACS analysis of human neutrophils incubated with serum from a xenomouse (A195-2) immunized with human L-selectin and labeled with an antibody immunoreactive with human light chain kappa region.

The stained, washed neutrophils were analyzed by FACS. The results for antiserum from xenomouse A195-2 are shown in FIGS. 8 and 9.

These results show the presence of antibodies in immunized xenomouse serum which contain fully human variable regions immunoreactive with L-selectin. The negative control antiserum from mice immunized with gp39 does not contain antibodies reactive against human neutrophils. Serum from A195-2 (immunized with L-selectin-expressing cells) contains antibodies binding to human neutrophils detectable with a goat antimouse IgG (FIG. 8), which immunoreacts with heavy chain protein composed of fully human variable regions and mouse γ constant regions. Staining with anti L-selectin xenomouse antisera detected with a mouse monoclonal antibody against human kappa is shown in FIG. 9, showing the presence of fully human kappa light chain.

As explained above, these antibodies containing human variable regions are readily convertible to fully human antibodies. For example, using hybridomas secreting these antibodies, the cDNAs encoding them can be obtained. By amplifying the genes encoding human V regions using primers containing restriction enzyme recognition sites and cloning them into plasmids containing the coding sequences for human constant regions as described by Queen, et al., *Proc Natl Acad Sci* (1989) 86:10029, genes encoding the fully human antibodies can be obtained for recombinant production.

EXAMPLE 6
Human Antibodies Against Human gp39 gp39 (the ligand for CD40) is expressed on activated human CD4+ T cells. The sera of xenomice immunized with recombinant gp39 according to this example contained antibodies immunospecific for gp39 with fully human variable regions; the sera contained fully human IgM antibodies and chimeric IgG antibodies containing human variable regions and murine constant heavy chain γ region.

Figure 10:
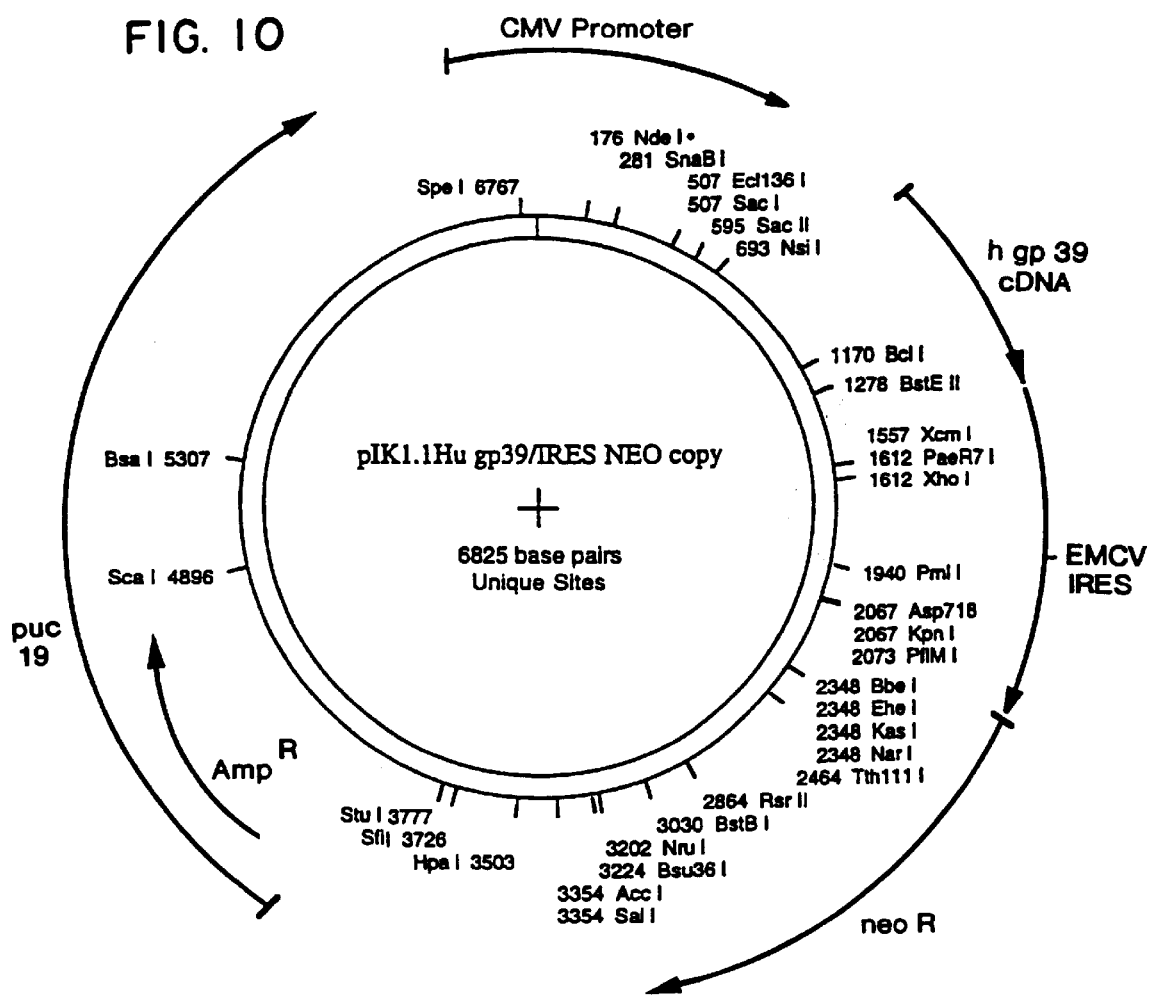
FIG. 10 is a diagram of a plasmid used to transfect mammalian cells to effect the production of the human protein gp39.

The antigen consisted of stable transfectants of 300.19 cells or of CHO cells expressing gp39 cDNA cloned into the mammalian expression vector P1K1.HUgp39/IRES NEO as shown in FIG. 10. CHO cells were split 1:10 prior to transfection in DMEM 4.5 g/l glucose, 10% FBS, 2 mM glutamine, MEM, NEAA supplemented with additional glycine, hypoxanthine and thymidine. The cells were cotransfected with the gp39 vector at 9 µg/10 cm plate (6×10$^5$ cells) and the DHFR expressing vector pSV2DHFRs (Subranani et al. *Mol Cell Biol* (1981) 9:854) at 1 µg/10 cm plate using calcium phosphate transfection. 24 hours later the cells were split 1:10 into the original medium containing G418 at 0.6 mg/ml. Cells producing gp39 were sorted by FACS using an anti-gp39 antibody.

Mice grouped as described in Example 1 were immunized with 300.19 cells expressing gp39 using a primary immunization subcutaneously at the base of the neck and with secondary intraperitoneal injections every 2–3 weeks. Sera were harvested as described in Example 1 for the ELISA assay. The ELISA procedure was conducted substantially as set forth in Example 1; the microtiter plates were coated with CHOD-gp39 cells grown in a 100 mm dish in DMEM, 4.5 g/l glucose, 10% FCS, 4 mM glutamine, and nonessential amino acid (NEAA) solution for MEM (100×). On the day preceding the ELISA assay, the cells were trypsinized and plated into 96-well filtration plates at 10$^5$ cells/200 µl well and incubated at 37° C. overnight. The positive controls were mouse antihuman gp39; negative controls were antisera from mice immunized with an antigen other than gp39. 50 µl of sample were used for each assay. The remainder of the assay is as described in Example 1.

Figure 11:
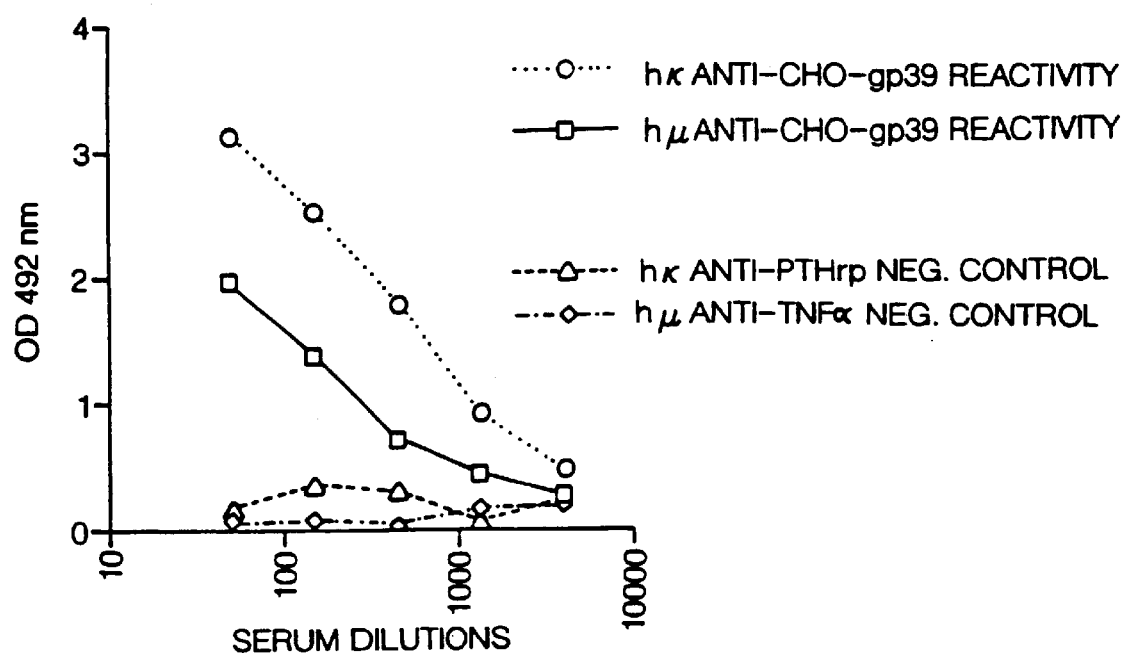
FIG. 11 represents the serum titration curve of mice immunized with CHO cells expressing human gp39. The antibodies detected in this ELISA must be immunoreactive with gp39 and contain human heavy chain $\mu$ constant regions or human kappa light chains.

The dilution curves for the sera obtained after 4 injections from mice immunized with gp39 expressed on CHO cells are shown in FIG. 11. As shown, the sera contained antihuman gp39 immunospecificity which is detectable with human kappa and human µ HRP-coupled antibodies.

In addition, the sera were tested for their ability to react with activated human T cells included in PBMC using FACS analysis. To prepare the PBMC, human peripheral blood was collected from normal volunteers with the addition of 100 unit/ml heparin. PBMC were isolated over Ficoll gradient and activated with 3 µg/ml PHA, 1 µg/ml PMA in IMDM plus 10% FBS plus 25 µM 2-mercaptoethanol for 4 hours. After washing, the PBMC were stained with mouse Mab against human CD4 labeled with FITC to permit separation of activated human T cells from unactivated cells.

The activated CD4+ and CD4− T cells were then analyzed by FACS using staining with either:

1) antiserum from a Xenomouse immunized with 300.19 cells producing gp39;

2) a positive control mouse Mab directed against α-CD40L (human gp39); and 3) a negative control antiserum from a Xenomouse immunized with TNF.

The detecting antibody in the FACS analysis was goat antimouse IgG (PE). The results are shown in FIG. 12.

Figure 12A:
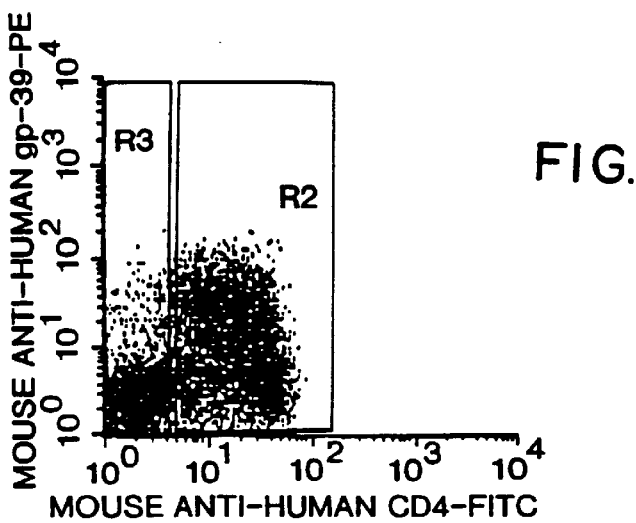
FIG. 12A shows the separation of human activated T cells into CD4+ and CD4− populations. Panel B shows the results of a FACS analysis of the activated CD4+ T cells with antibodies from the xenomouse immunized with gp39 which contain murine heavy chain γ constant regions; panel C shows the corresponding results with respect to CD4− populations.
Figure 12B:
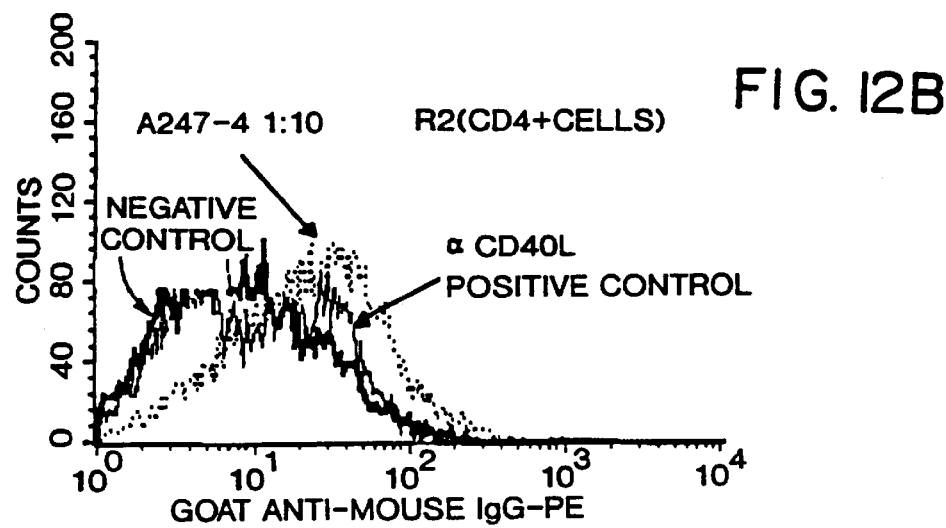
FIGS. 12(A–C) shows the results of a FACS analysis of antibodies from a xenomouse (labeled A247-4) immunized with human gp39 reacted with activated human T cells.
Figure 12C:
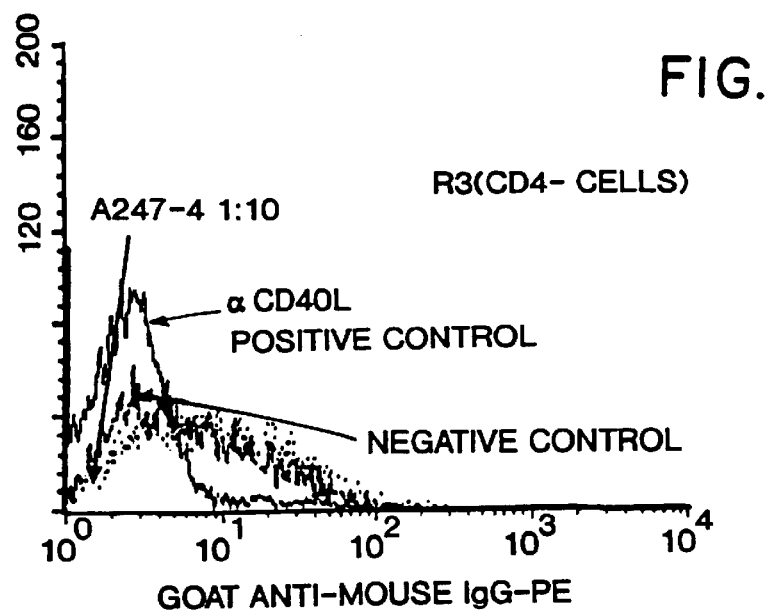

As shown in FIG. 12A, CD4+ (R2) and CD4− (R3) cells were separated prior to FACS analysis. Panel B shows the results for CD4+ cells and shows that sera from mice immunized with gp39 (labeled A247-4 in the figure) reacted with these activated PBMC; panel C shows that these sera did not react with CD4− cells. These antibodies carried immune heavy chain γ constant regions. The results of panels B and C confirm that the TNF-injected xenomouse did not make antibodies against activated human T cells.

EXAMPLE 7
Preparation of High-Affinity Human Mabs Against Tetanus Toxin

The antibodies prepared in this example were secreted by hybridomas obtained by immortalizing B cells from xenomice immunized with tetanus toxin. The immunization protocol was similar to that set forth in Example 1 using 50 µg tetanus toxin emulsified in complete Freund's adjuvant for intraperitoneal primary immunization followed by subsequent intraperitoneal injections with antigen incorporated into incomplete Freund's adjuvant. The mice received a total of 4 injections 2–3 weeks apart.

After acceptable serum titers of antitetanus toxinC (anti-TTC) were obtained, a final dose of antigen in PBS was given 4 days before the animals were sacrificed and the spleens harvested for fusion.

The spleen cells were fused with myeloma cells P3X63-Ag8.653 as described by Galfre, G. and Milstein, C. *Methods in Enzymology* (1981) 73:3–46.

After fusion the cells were resuspended in DMEM, 15% FCS, containing HAT supplemented with glutamine, pen/strep for culture at 37° C. and 10% $CO_2$. The cells were plated in microtiter trays and maintained in HAT-supplemented medium for two weeks before transfer to HT-supplemented media. Supernatants from wells containing hybridomas were collected for a primary screen using an ELISA.

Figure 15:
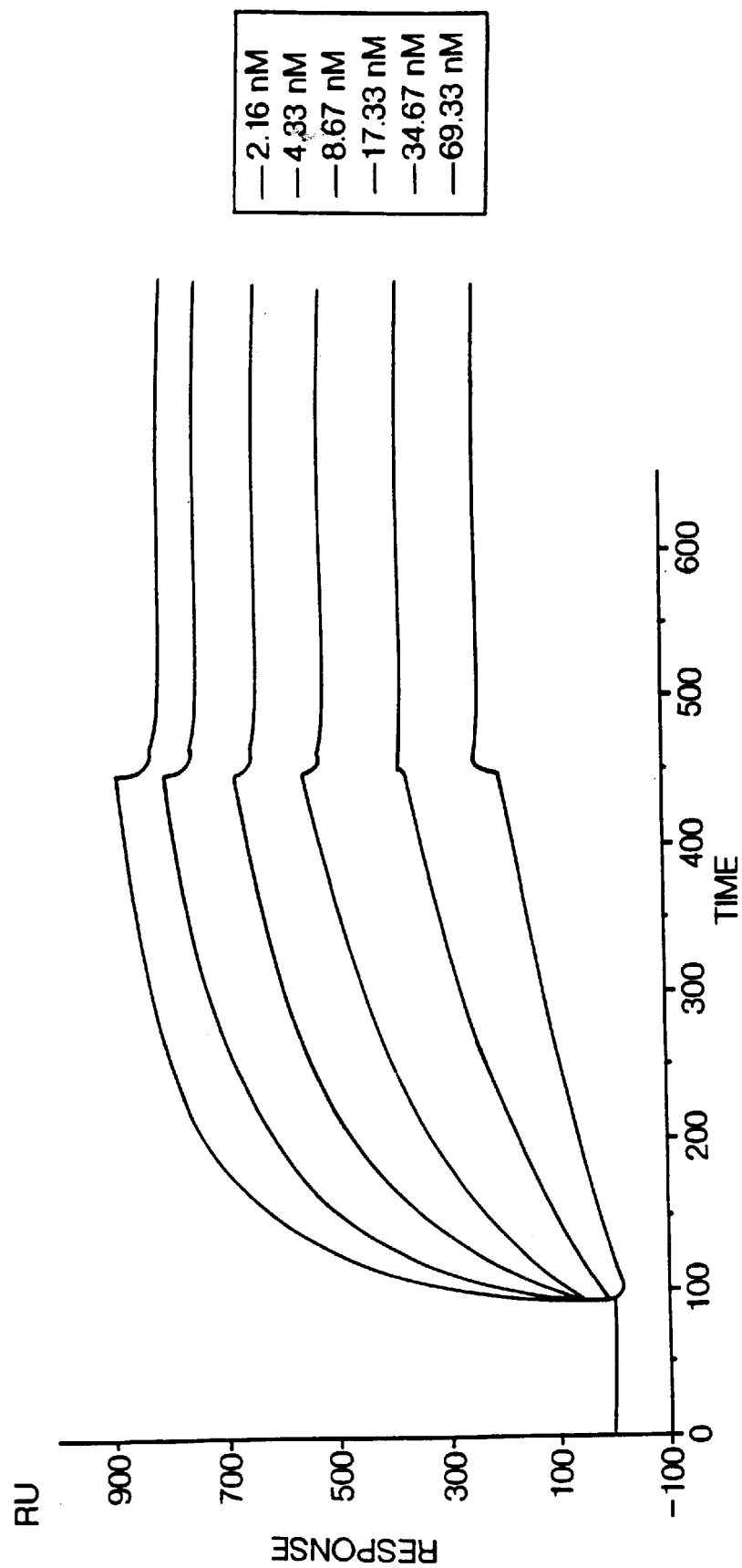
FIG. 15 shows binding curves for various concentrations of the K4.1 monoclonal antibody in a determination of the affinity of the monoclonal with its antigen in a BIAcore instrument.

The ELISA was conducted as described in Example 1 wherein the antigen coating consisted of 100 µl/well of tetanus toxin C (TTC) protein at 2 mg/ml in coating buffer, The chips are used to determine binding affinities by determining $k_a$ and $k_b$ (the association and dissociation rate constants) for the antibody with respect to the immobilized TTC. The association rate constant is measured over six minutes at a flow rate of 5 µl/min. at different concentrations of K4.1 Mab in the range of 2.16 nm–69.33 nm. The dissociation rate constant is measured at a constant buffer flow rate of 5 µl/min after completion of the antibody injection. The raw data are graphed in FIG. 15 and the calculated results are shown in Table 1.

TABLE 1

Kinetic Constants of K4.1 Measured Using the BIAcore on Two Different Surfaces

| Immobilized tetanus toxinC | K4.1 conc. range nM | Association rate $ka(10^5\ M^{-1}s^{-1})$ | Dissociation rate $kd(10^5s^{-1})$ | Binding constant $KA(M^{-1})$ = ka/kd | Dissociation constant $KD(M)$ = kd/ka |
|---|---|---|---|---|---|
| 5931 RU | 4.3–34.7 | 6.47 ± 1.05 | 4.02 ± 1.42 | $1.6 \times 10^{10}$ | $0.62 \times 10^{-10}$ |
| 868 RU | 4.3–34.7 | 7.19 ± 2.18 | 2.02 ± 1.01 | $3.5 \times 10^{10}$ | $0.28 \times 10^{-10}$ | followed by incubation at 4° C. overnight or at 37° C. for two hours. In the primary ELISA, HRP-conjugated goat antimouse IgG at 1/2000 was used in addition to HRP mouse antihuman IgM as described in Example 1. Two hybridomas that secreted anti-TTC according to the ELISA assay, clone D5.1 and clone K4.1 were used for further analysis.

Figure 13:
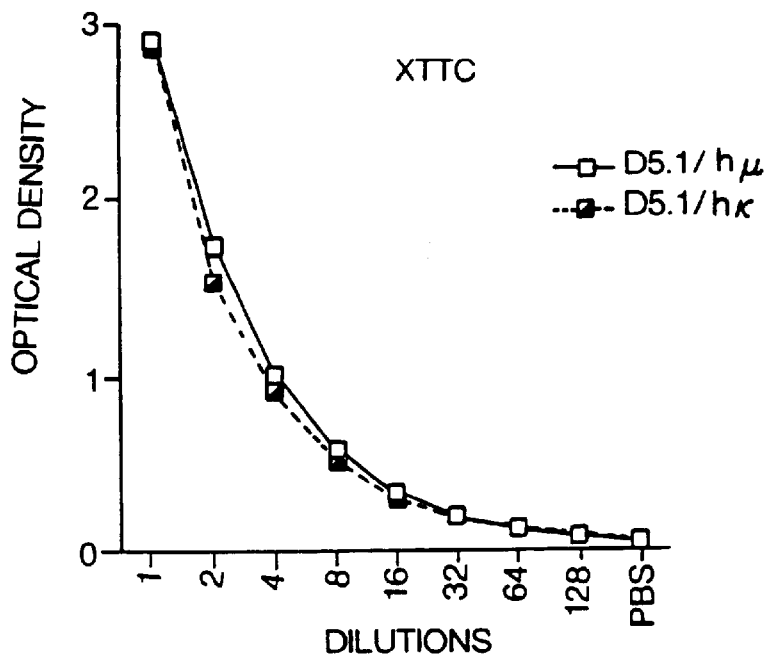
FIG. 13 is a titration curve with respect to monoclonal antibodies secreted by the hybridoma clone D5.1. This clone is obtained from a xenomouse immunized with tetanus toxin C (TTC) and contains human kappa light chain and human $\mu$ constant region in the heavy chain.
Figure 14:
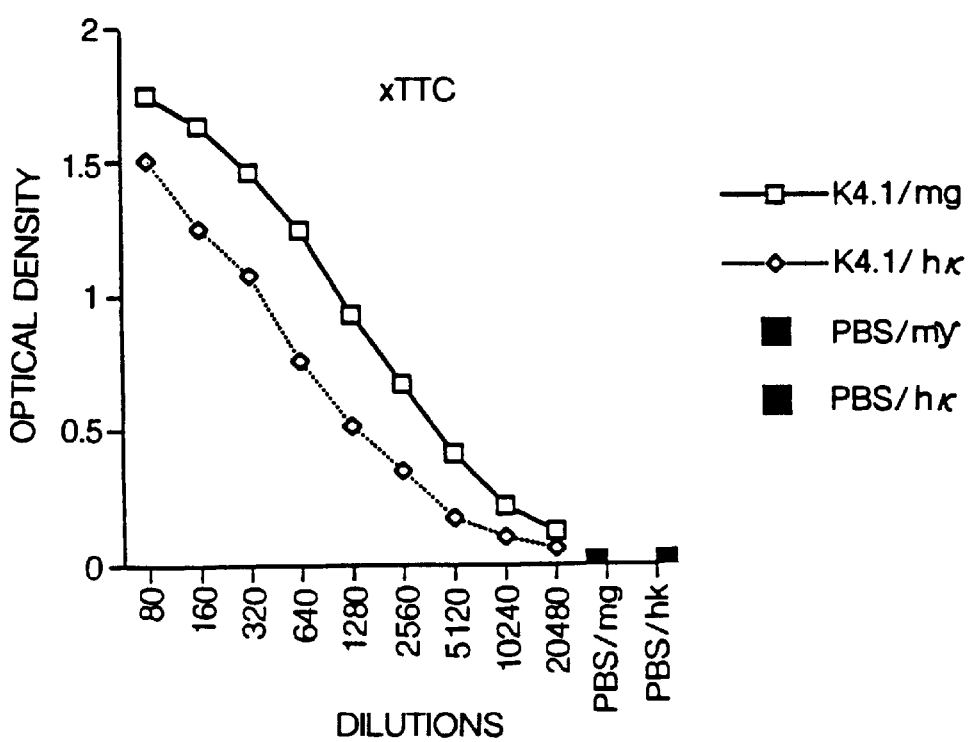
FIG. 14 is a titration curve with respect to the hybridoma supernatant from clone K4.1. This hybridoma clone is obtained from a xenomouse immunized with TTC and contains human kappa light chain and heavy chain having the murine γ constant region.

As shown in FIG. 13, clone D5.1 secretes fully human anti-TTC which is detectable using HRP-conjugated anti-human µ and HRP-conjugated antihuman kappa. FIG. 14 shows that clone K4.1 secretes anti-TTC which is immunoreactive with antimurine γ and antihuman kappa HRP-conjugated antibodies. Thus, clone K4.1 provides anti-TTC with human variable regions and a murine constant heavy chain γ region.

The antibodies secreted by D5.1 and K4.1 did not immunoreact in ELISAs using TNFα, IL-6, or IL-8 as immobilized antigen under conditions where positive controls (sera from xenomice immunized with TNFα, IL-6 and IL-8 respectively) showed positive ELISA results.

The affinity of the monoclonal antibodies secreted by K4.1 for TTC antigen was determined using commercially available reagents and instrumentation. BIAcore Instrument, CM5 sensor chips, surfactant P20 and the amine coupling kit were purchased from Pharmacia Biosensor (Piscataway, N.J.). TTC was immobilized at two levels of antigen density on the surface of the sensor chips according to the manufacturer's instructions. Briefly, after washing and equilibrating the instrument with buffer containing surfactant, the surfaces were activated and the TCC was immobilized.

For high antigen density, the surface was activated with 35 µl of equal volumes 0.1 M NHS and 0.1 M EDC injected across the surface followed by 30 µl of TTC fragment at 100 µg/ml in 10 mM sodium acetate buffer pH 5.0. The surface was blocked by injecting 35 µl 1 M ethanolamine and washed to remove noncovalently bound TCC using 5 µl 0.1 M HCl. The entire immobilization procedure was conducted with a continuous flow of buffer at 5 µl/min. This results in about 7500–8500 response units (RU) of TTC per chip. (1000 RU corresponds to about 1 ng of protein per $mm^2$.)

For chips with low antigen density, the procedure utilizes 15 µl rather than 30 µl of TTC, resulting in chips containing 550–950 RU.

Chips could be regenerated after use in single determinations by injecting 10 µl formal or $MgCl_2$.

As shown, the K4.1 antibody has a binding constant for TTC somewhat larger than $10^{10}$ 1/mol.

The complete nucleotide sequence of the cDNAs encoding the heavy and light chains of the K4.1 and D5.1 monoclonals were determined as shown in FIGS. 16–19. PolyA mRNA was isolated from about $10^6$ hybridoma cells and used to generate cDNA using random hexamers as primers. Portions of the product were amplified by PCR using the appropriate primers.

Both cell lines were known to provide human kappa light chains; for PCR amplification of light chain encoding cDNA, the primers used were HKP1

(5'-CTCTGTGACACTCTCCTGGGAGTT-3')   (SEQ ID NO: 1)

for priming from the constant region terminus and two oligos, used in equal amounts to prime from the variable segments: B3

(5'-CCACCATCAACTGCAAGTCCAGCCA-3')   (SEQ ID NO: 2)

and B2/B1

(5'-GAAACGACACTCACGCAGTCTCCAGC-3'(SEQ ID NO: 3).

For amplification of the heavy chain from K4.1 (which contains the murine γ1 constant region), the primers were MG-24Vi for the human variable regions: 5'-CAGGTGCAGCTGGAGCAGTCiGG-3' (SEQ ID NO: 4) which, with inosine as shown recognizes the human variable regions $V_{H1-2}$, $V_{H1-3}$, $V_{H4}$ and $V_{H6}$, and from the constant region MG-25 i.e., 5'-GCACACCGCTGGACAGGGATCCAiAGTTTC-3' (SEQ ID NO: 5), which, containing inosine as shown recognizes murine γ1, γ2A, γ2B, and γ3.

For amplification of the heavy chain of the antibody derived from D5.1 (which contains the human µ constant region), MG-24VI was used to prime from the variable and µP1 (5'-TTTTCTTTGTTGCCGTTGGGGTGC-3') (SEQ ID NO: 6) was used as prime from the constant region terminus.

Figure 16A:
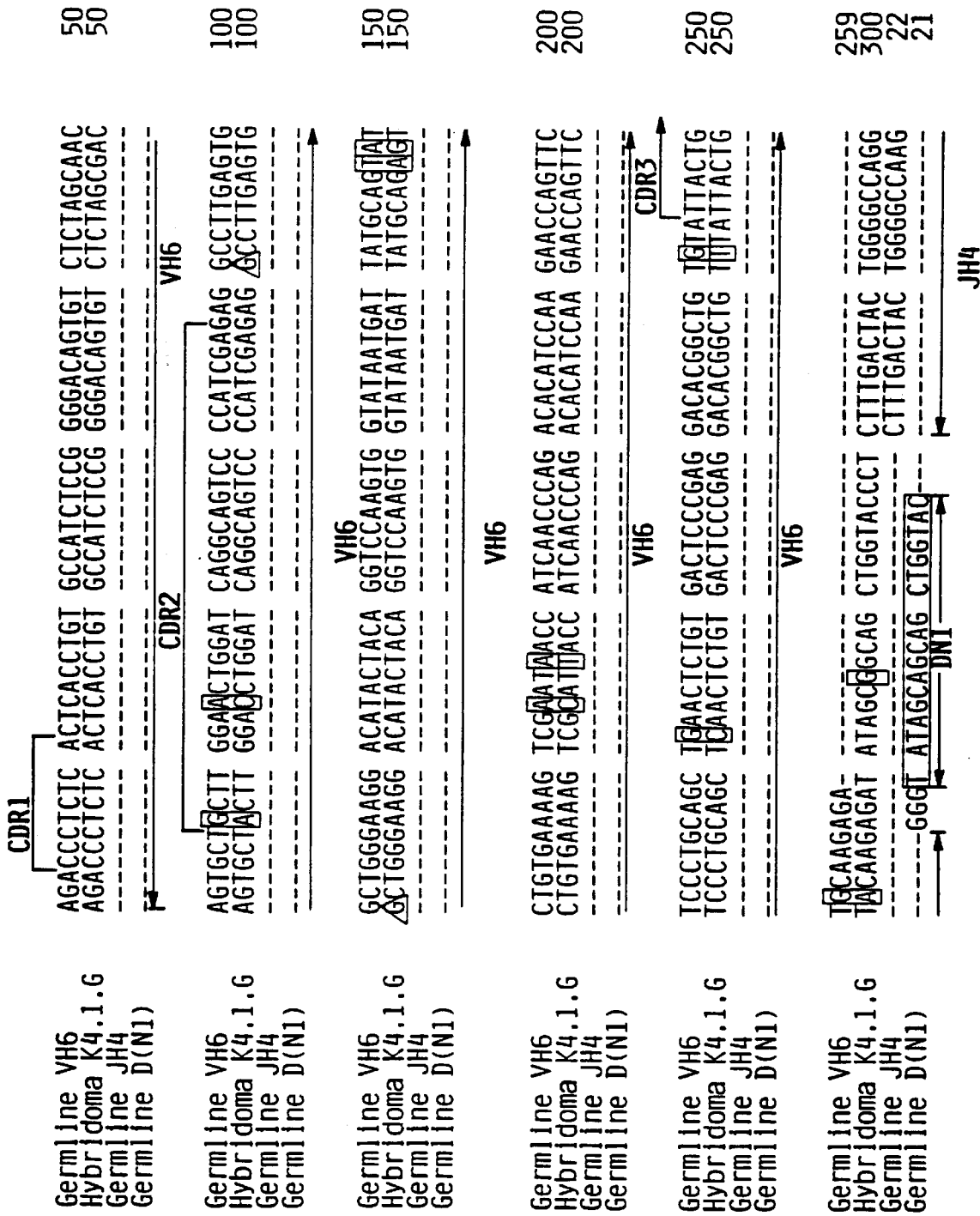
FIG. 16 shows the complete nucleotide sequence of the heavy chain from the antibody secreted by K4.1 (SEQ ID NOS 7–10).
Figure 16B:
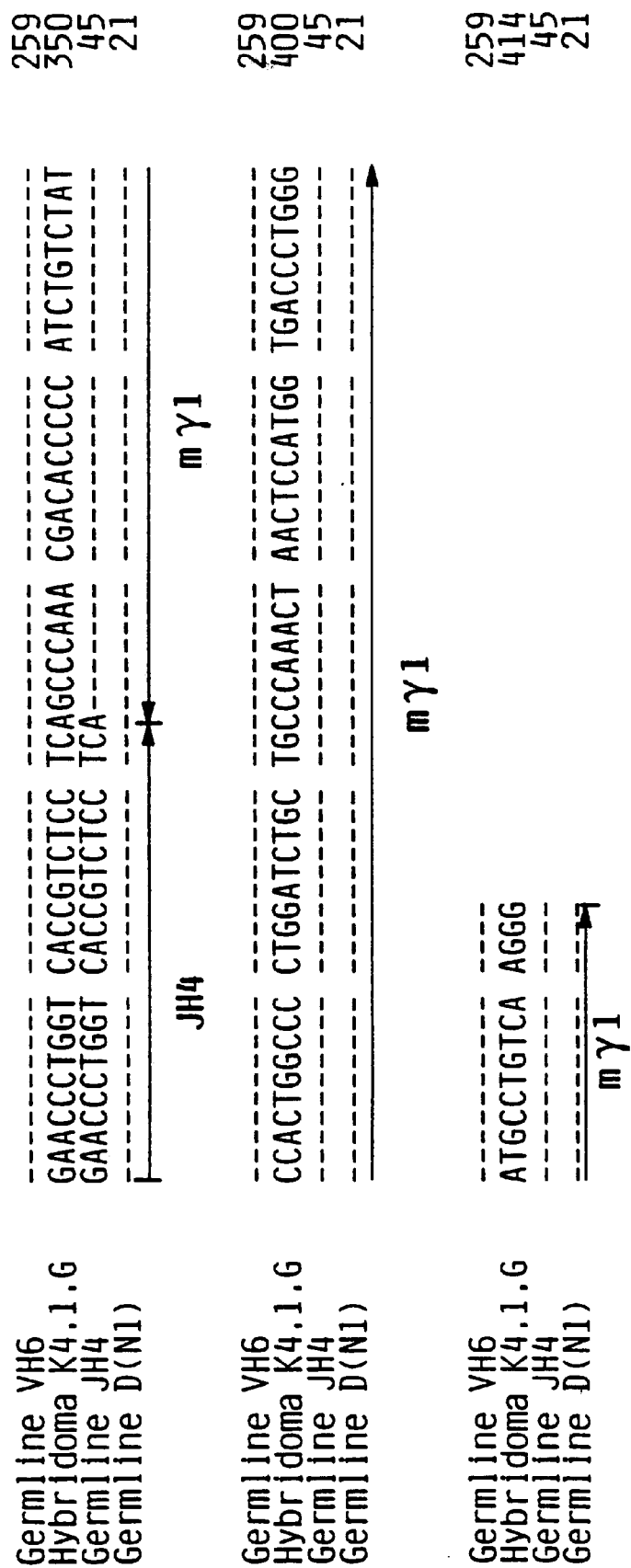

Turning first to the results shown in FIG. 16 representing the heavy chain of the Mab secreted by K4.1, the sequence shows the presence of the human variable segment VH6, the human diversity region DN1, and the human joining segment JH4 linked to the murine γ1 constant region. Nine base-pair mutations from the published germline sequence were present in the variable region, two of them within CDR2. One mutation was observed in the D segment. Three nongermline nucleotide additions were present in the $D_H$-$J_H$ junction.

Figure 17:
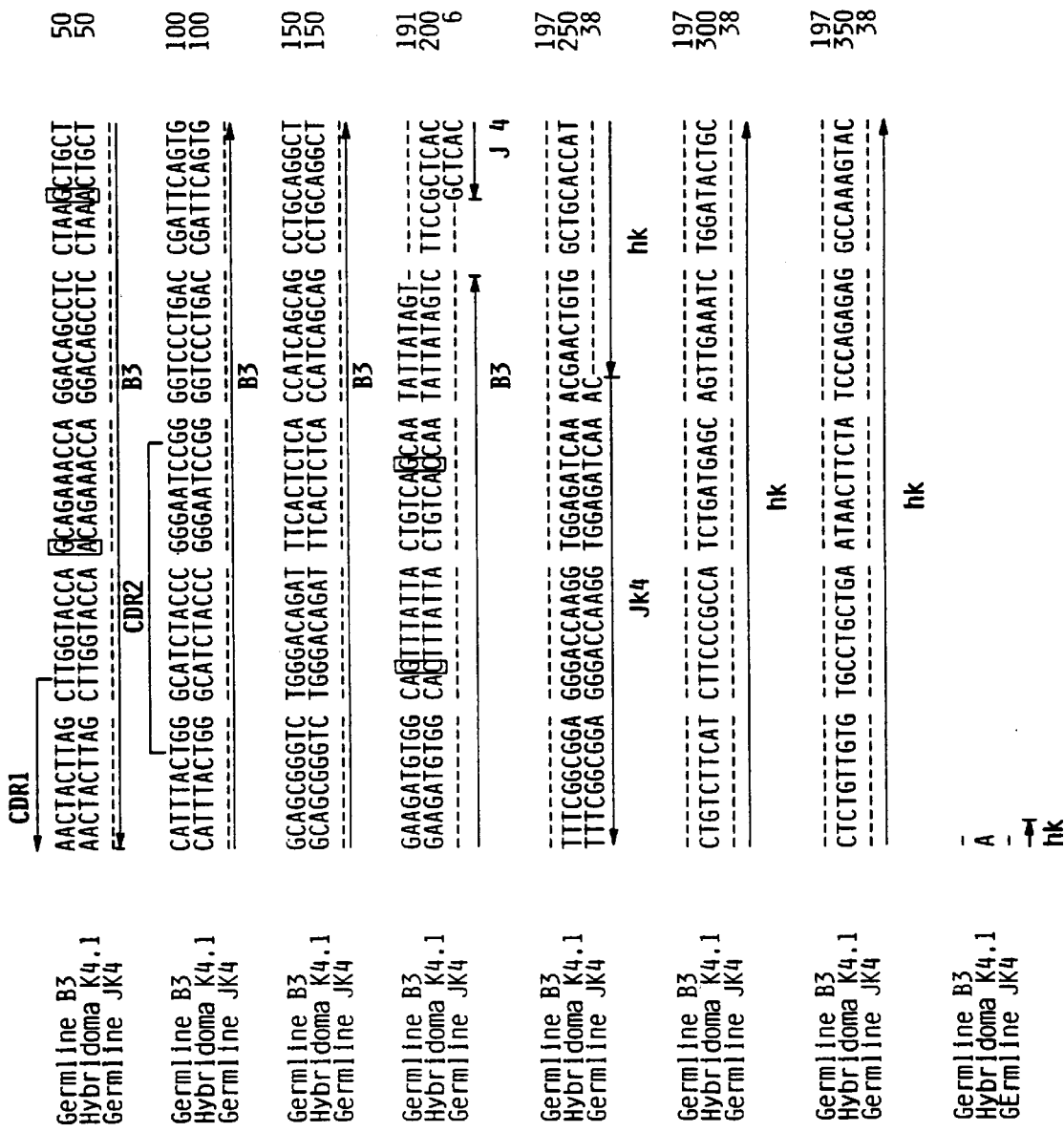
FIG. 17 shows the complete nucleotide sequence of the light chain from the antibody secreted by K4.1 (SEQ ID NOS 11–13).

Referring to FIG. 17 which shows the light chain of the K4.1 antibody, analysis shows the presence of the human kappa variable region B3 and joining region JK4. Eight nucleotides are missing from B3 at the $V_K$-$J_K$ junction and four mutations were found in the variable region. Five nongermline nucleotide additions were present at the $V_K$-$J_K$ junction.

Figure 18B:
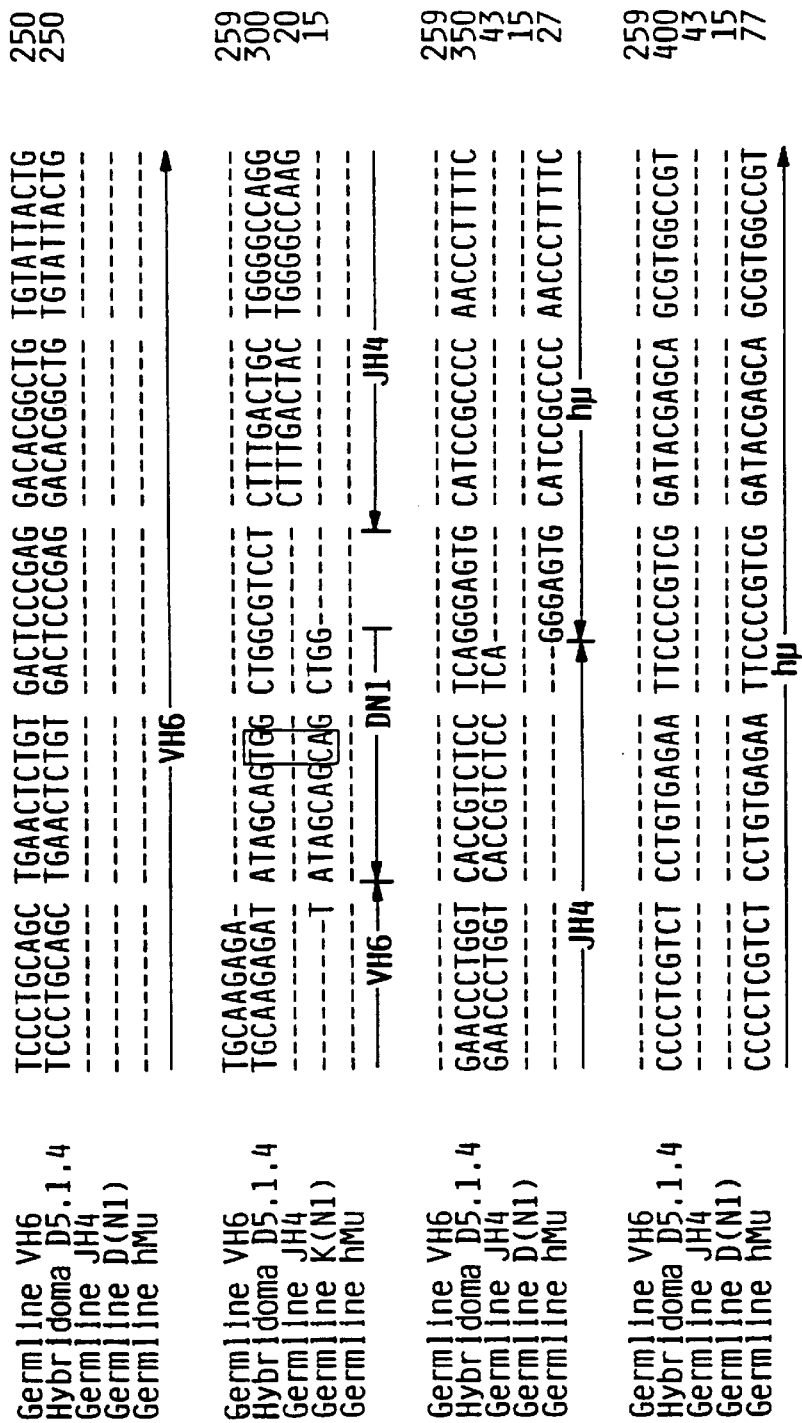
FIG. 18 shows the complete nucleotide sequence of the heavy chain from the antibody secreted by D5.1 (SEQ ID NOS 14–17).

Referring now to FIG. 18 which sets forth the sequence for the heavy chain of the antibody secreted by clone D5.1, this shows the heavy chain is comprised of the human variable fragment VH6, the human diversity region DN1 and the human joining segment JH4 linked to the human $\mu$ constant region. There were two base-pair mutations from the germline sequence in the variable region, neither within the CDRs. Two additional mutations were in the D segment and six nongermline nucleotide additions were present at the $D_H$-$J_H$ junction.

Finally, referring to FIG. 19 which presents the light chain of the antibody secreted by D5.1, the human kappa variable region B3 and human kappa joining region JK3 are shown. There are nine base-pair differences from the germline sequences, three falling within CDR1.

Cloning of Human Heavy Chain Locus Using Yeast Artificial Chromosomes

A. Production of Yeast Artificial Chromosome (YAC) Containing Human Heavy Chain

An SpeI fragment, spanning the human heavy chain VH6-D-J-C$\mu$-C$\delta$ region (Berman et al. (1988), *EMBO J.* 7: 727–738; see FIG. 20) is isolated from a human YAC library (Burke, et al., *Science*, 236; 806–812) using DNA probes described by Berman et al. (1988) *EMBO J.* 7:727–738. One clone is obtained which is estimated to be about 100 kb. The isolated YAC clone is characterized by pulsed-field gel electrophoresis (Burke et al., supra; Brownstein et al., *Science*, 244: 1348–1351), using radiolabelled probes for the human heavy chain (Berman et al., supra).

B. Introduction of YAC Clones Into Embryos or ES Cells

High molecular weight DNA is prepared in agarose plugs from yeast cells containing the YAC of interest (i.e., a YAC containing the aforementioned SpeI fragment from the IgH locus). The DNA is size-fractionated on a CHEF gel apparatus and the YAC band is cut out of the low melting point agarose gel. The gel fragment is equilibrated with polyamines and then melted and treated with agarase to digest the agarose. The polyamine-coated DNA is then injected into the male pronucleus of fertilized mouse embryos which are then surgically introduced into the uterus of a psueudopregnant female as described above. The transgenic nature of the newborns is analyzed by a slot-blot of DNA isolated from tails and the production of human heavy chain is analyzed by obtaining a small amount of serum and testing it for the presence of Ig chains with rabbit anti-human antibodies.

As an alternative to microinjection, YAC DNA is transferred into murine ES cells by ES cell:yeast protoplast fusion (Traver et al., (1989) *Proc. Natl. Acad. Sci., USA*, 86: 5898–5902; Pachnis et al., (1990), *ibid* 87; 5109–5113). First, the neomycin-resistance gene from pMClNeo or HPRT or other mammalian selectable marker and a yeast selectable marker are inserted into nonessential YAC vector sequences in a plasmid. This construct is used to transform a yeast strain containing the IgH YAC, and pMClNeo (or other selectable marker) is integrated into vector sequences of the IgH YAC by homologous recombination. The modified YAC is then transferred into an ES cell by protoplast fusion (Traver et al. (1989); Pachnis et al., 1990), and resulting G418-resistant ES cells (or exhibiting another selectable phenotype) which contain the intact human IgH sequences are used to generate chimeric mice. Alternatively, a purified YAC is transfected, for example by lipofection or calcium phosphate-mediated DNA transfer, into ES cells.

Production of Human IG by Chimeric Mice by Introduction of Human IG Using Homologous Recombination As an alternative approach to that set forth in Examples I–VI, human Ig genes are introduced into the mouse Ig locus by replacing mouse heavy and light chain immunoglobulin loci directly with fragments of the human heavy and light chain loci using homologous recombination. This is followed by the generation of chimeric transgenic animals in which the embryonic stem-cell derived cells contribute to the germ line.

A. Construction of Human Heavy Chain Replacement Vector

Figure 20A:
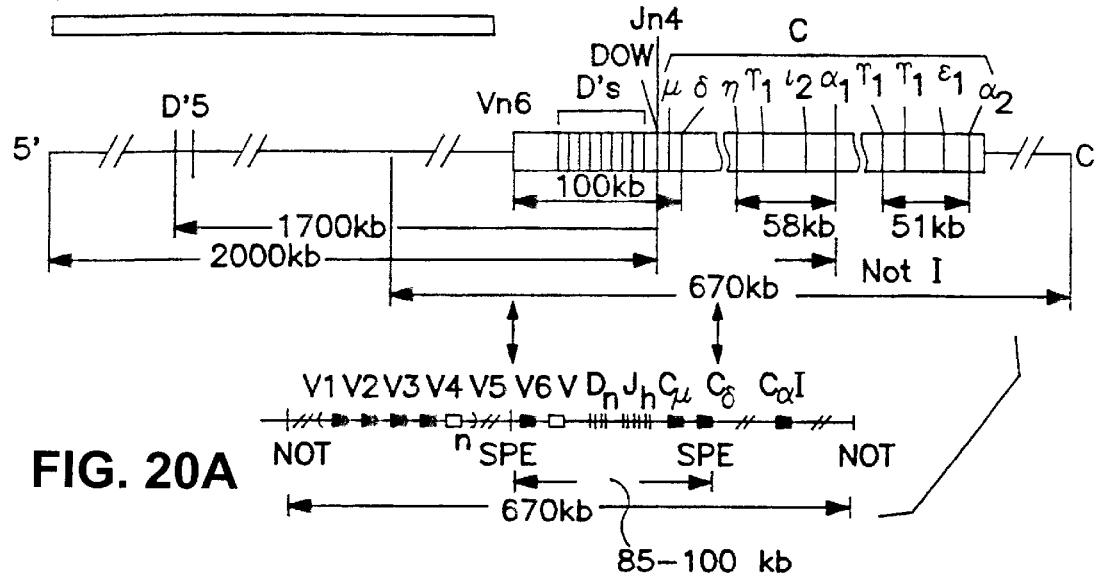
FIGS. 20(A–C) shows diagrams of the human immunoglobulin heavy chain locus, and a human heavy chain replacement YAC vector.
Figure 20B:
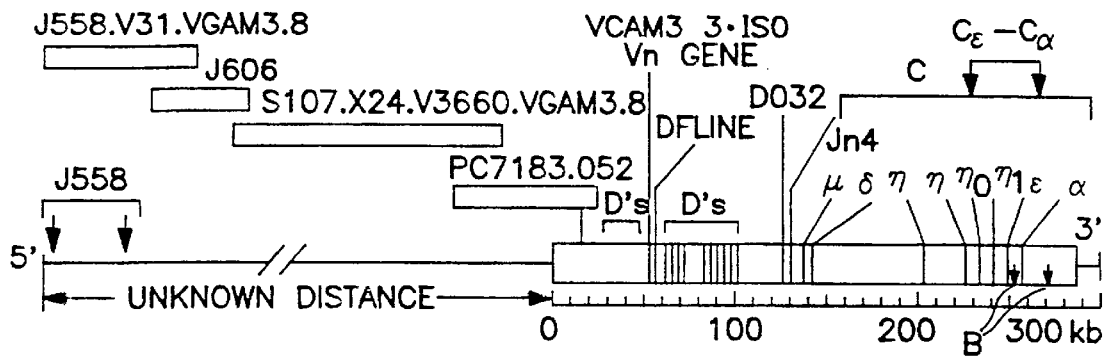
Figure 20C:
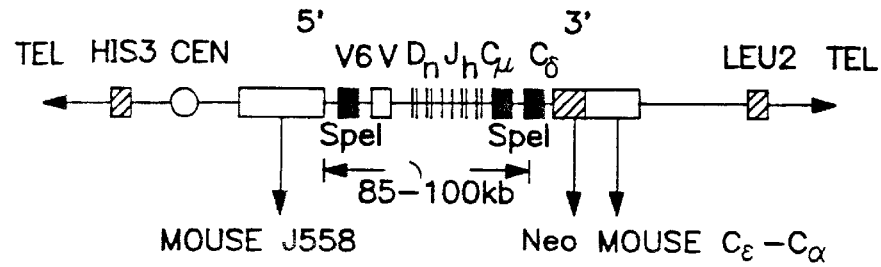

The replacing human sequences include the SpeI 100 kb fragment of genomic DNA which encompasses the human VH6-D-J-C$\mu$-C$\delta$ heavy chain region isolated from a human-YAC library as described before. The flanking mouse heavy chain sequences, which drive the homologous recombination replacement event, contain a 10 kb BamHI fragment of the mouse C$\epsilon$-C$\alpha$ heavy chain and a 5' J558 fragment comprising the 5' half of the J558 fragment of the mouse heavy chain variable region, at the 3' and 5' ends of the human sequences, respectively (FIG. 20). These mouse sequences are isolated from a mouse embryo genomic library using the probes described in Tucker et al. (1981), *PNAS USA*. 78; 7684–7688 and Blankenstein and Krawinkel (1987, supra), respectively. The 1150 bp XhoI to BamHI fragment, containing a neomycin-resistance gene driven by the Herpes simplex virus thymidine kinase gene (HSV-tk) promoter and a polyoma enhancer is isolated from pMClNeo (Koller and Smithies, 1989, supra). A synthetic adaptor is added onto this fragment to convert the XhoI end into a BamHI end and the resulting fragment is joined to the BamHI mouse C$\epsilon$-C$\alpha$ in a plasmid.

From the YAC clone containing the human heavy chain locus, DNA sequences from each end of the insert are recovered either by inverse PCR (Silverman et al. (1989), *PNAS*, 86:7485–7489), or by plasmid rescue in *E. coli*. Burke et al., (1987); Garza et al. (1989) *Science*, 246:641–646; Traver et al., 1989) (see FIG. 20). The isolated human sequence from the 5'V6 end of the YAC is ligated to the mouse J558 sequence in a plasmid and likewise, the human sequence derived from the 3'Cd end of the YAC is ligated to the Neo gene in the plasmid containing Neo and mouse C$\epsilon$-C$\alpha$ described above. The human V6-mouse J558 segment is now subcloned into a half-YAC cloning vector that includes a yeast selectable marker (HIS3) not present in the original IgH YAC, a centromere (CEN) and a single telomere (TEL). The human C$\delta$-Neo-mouse C$\epsilon$-C$\alpha$ is likewise subcloned into a separate half-YAC vector with a different yeast selectable marker (LEU2) and a single TEL. The half-YAC vector containing the human V6 DNA is linearized and used to transform a yeast strain that is deleted for the chromosomal HIS3 and LEU2 loci and which carries the IgH YAC. Selection for histidine-prototrophy gives rise to yeast colonies that have undergone homologous recombination between the human V6 DNA sequences and contain a recombinant YAC. The half-YAC vector containing the human Cδ DNA is then linearized and used to transform the yeast strain generated in the previous step. Selection for leucine-prototrophy results in a yeast strain containing the complete IgH replacement YAC (see FIG. 20). Preferably, both targeting events are performed in a single transformation step, selecting simultaneously for leucine and histidine prototrophy. This is particularly useful when the original centric and acentric YAC arms are in opposite orientation to that shown in FIG. 20. This YAC is isolated and introduced into ES cells by microinjection as described previously for embryos.

What is claimed is:

1. A method for producing a human IgM comprising a nonchimeric variable region, wherein said immunoglobulin is specific for a desired antigen, wherein said method comprises the steps of:

(a) administering said antigen or an immunogenic portion thereof to a transgenic mouse under conditions to stimulate an immune response, whereby said animal produces B cells that produce said immunoglobulin specific for said antigen, wherein the genome of said transgenic mouse is characterized by inactivated endogenous immunoglobulin heavy chain loci in which all of the J segment genes are deleted to prevent rearrangement of the loci and to prevent formation of a transcript of a rearranged immunoglobulin heavy chain locus, and by inactivated endogenous immunoglobulin light chain loci in which genes are deleted to prevent rearrangement of the loci and to prevent formation of a transcript of a rearranged immunoglobulin light chain locus, and wherein said genome of said transgenic mouse further comprises a DNA fragment of a human immunoglobulin heavy chain locus, the fragment being a SpeI-SpeI fragment commencing from the VH6 gene and continuing through the human D segment genes, human J segment genes and human constant region genes and into the Cδ gene of that locus, wherein said SpeI-SpeI fragment does not include a gamma constant region, and further comprises a fragment of human chromosome 2, said fragment comprising Vκ, Jκ and Cκ gene segments of a human immunoglobulin kappa light chain locus, and (b) recovering said immunoglobulin, provided that if said immunoglobulin comprises a human constant region, said human constant region is a human mu constant region or a human kappa constant region, or both.

2. A method for producing an antigen binding fragment of a human IgM, said fragment comprising a nonchimeric variable region, wherein said fragment is specific for a desired antigen, wherein said method comprises the steps of:

(a) administering said antigen or an immunogenic portion thereof to a transgenic mouse under conditions to stimulate an immune response, whereby said animal produces B cells that produce said immunoglobulin specific for said antigen, wherein the genome of said transgenic mouse is characterized by inactivated endogenous immunoglobulin heavy chain loci in which all of the J segment genes are deleted to prevent rearrangement of the loci and to prevent formation of a transcript of a rearranged immunoglobulin heavy chain locus, by inactivated endogenous immunoglobulin light chain loci in which one or more genes are deleted to prevent rearrangement of the loci and to prevent formation of a transcript of a rearranged immunoglobulin light chain locus, and wherein said genome of said transgenic mouse further comprises a DNA fragment of a human immunoglobulin heavy chain locus, the fragment being a SpeI-SpeI fragment commencing from the VH6 gene and continuing through the human D segment genes, human J segment genes and human constant region genes and into the Cδ gene of that locus, wherein said SpeI-SpeI fragment does not include a gamma constant region, and further comprises a fragment of human chromosome 2, said fragment comprising Vκ, Jκ and Cκ gene segments of a human immunoglobulin kappa light chain locus, (b) recovering said immunoglobulin specific for said antigen, and (c) producing an antigen-binding fragment from said immunoglobulin recovered in step (b).

3. The method according to claim 1 or 2, wherein said recovering step comprises recovering polyclonal immunoglobulin from said transgenic mouse.

4. The method according to claim 1 or 2, wherein said recovering step comprises immortalizing B cells from said transgenic mouse immunized with said antigen, screening the resulting immortalized cells for the secretion of said immunoglobulin specific for said antigen, and (a) recovering immunoglobulin secreted by said immortalized B cells, or (b) recovering the genes encoding at least the variable region of said immunoglobulin from the immortalized B cells, and optionally modifying said genes to encode a modified immunoglobulin;

(c) expressing said genes or modified forms thereof to produce said immunoglobulin or said modified immunoglobulin; and (d) recovering said immunoglobulin or said modified immunoglobulin.

* * * * *

SEQUENCE LISTING

```
<160> NUMBER OF SEQ ID NOS: 22

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 1
ctctgtgaca ctctcctggg agtt                                          24

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 2
ccaccatcaa ctgcaagtcc agcca                                         25

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 3
gaaacgacac tcacgcagtc tccagc                                        26

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (21)
<223> OTHER INFORMATION: Inosine

<400> SEQUENCE: 4
caggtgcagc tggagcagtc ngg                                           23

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (24)
<223> OTHER INFORMATION: Inosine

<400> SEQUENCE: 5
```
gcacaccgct ggacagggat ccanagtttc                            30

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 6
ttttctttgt tgccgttggg gtgc                                  24

<210> SEQ ID NO 7
<211> LENGTH: 259
<212> TYPE: DNA
<213> ORGANISM: Homo sapiens

<400> SEQUENCE: 7
agaccctctc actcacctgt gccatctccg gggacagtgt ctctagcaac agtgctgctt    60
ggaactggat caggcagtcc ccatcgagag gccttgagtg ctgggaagg acatactaca    120 ggtccaagtg gtataatgat tatgcagtat ctgtgaaaag tcgaataacc atcaacccag   180
acacatccaa gaaccagttc tccctgcagc tgaactctgt gactcccgag gacacggctg   240
tgtattactg tgcaagaga                                               259

<210> SEQ ID NO 8
<211> LENGTH: 414
<212> TYPE: DNA
<213> ORGANISM: Homo sapiens

<400> SEQUENCE: 8
agaccctctc actcacctgt gccatctccg gggacagtgt ctctagcgac agtgctactt    60
ggacctggat caggcagtcc ccatcgagag gccttgagtg ctgggaagg acatactaca    120 ggtccaagtg gtataatgat tatgcagagt ctgtgaaaag tcgcattacc atcaacccag   180
acacatccaa gaaccagttc tccctgcagc tcaactctgt gactcccgag gacacggctg   240
tttattactg tacaagagat atagcggcag ctggtaccct ctttgactac tggggccagg   300
gaaccctggt caccgtctcc tcagcccaaa cgacaccccc atctgtctat ccactggccc   360
ctggatctgc tgcccaaact aactccatgg tgaccctggg atgcctgtca aggg         414

<210> SEQ ID NO 9
<211> LENGTH: 43
<212> TYPE: DNA
<213> ORGANISM: Homo sapiens

<400> SEQUENCE: 9
ctttgactac tggggccaag gaaccctggt caccgtctcc tca                     43

<210> SEQ ID NO 10
<211> LENGTH: 21
<212> TYPE: DNA
<213> ORGANISM: Homo sapiens

<400> SEQUENCE: 10
gggtatagca gcagctggta c                                             21

<210> SEQ ID NO 11
<211> LENGTH: 189
<212> TYPE: DNA
<213> ORGANISM: Homo sapiens

<400> SEQUENCE: 11

```
aactacttag cttggtacca gcagaaacca ggacagcctc ctaagctgct catttactgg      60
gcatctaccc gggaatccgg ggtccctgac cgattcagtg gcagcgggtc tgggacagat     120
ttcactctca ccatcagcag cctgcaggct gaagatgtgg cagtttatta ctgtcagcaa     180
tattatagt                                                             189
```

<210> SEQ ID NO 12
<211> LENGTH: 351
<212> TYPE: DNA
<213> ORGANISM: Homo sapiens

<400> SEQUENCE: 12

```
aactacttag cttggtacca acagaaacca ggacagcctc ctaaactgct catttactgg      60
gcatctaccc gggaatccgg ggtccctgac cgattcagtg gcagcgggtc tgggacagat     120
ttcactctca ccatcagcag cctgcaggct gaagatgtgg cactttatta ctgtcaccaa     180
tattatagtc ttccgctcac tttcggcgga gggaccaagg tggagatcaa acgaactgtg     240
gctgcaccat ctgtcttcat cttcccgcca tctgatgagc agttgaaatc tggatactgc     300
ctctgttgtg tgcctgctga ataacttcta tcccagagag gccaaagtac a              351
```

<210> SEQ ID NO 13
<211> LENGTH: 38
<212> TYPE: DNA
<213> ORGANISM: Homo sapiens

<400> SEQUENCE: 13

```
gctcactttc ggcggaggga ccaaggtgga gatcaaac                              38
```

<210> SEQ ID NO 14
<211> LENGTH: 302
<212> TYPE: DNA
<213> ORGANISM: Homo sapiens

<400> SEQUENCE: 14

```
gacatcgtga tgacccagtc tccagactcc ctggctgtgt ctctgggcga gagggccacc      60
atcaactgca agtccagcca gagtgtttta tacagctcca acaataagaa ctacttagct     120
tggtaccagc agaaaccagg acagcctcct aagctgctca tttactgggc atctacccgg     180
gaatccgggg tccctgaccg attcagtggc agcgggtctg ggacagattt cactctcacc     240
atcagcagcc tgcaggctga agatgtggca gtttattact gtcagcaata ttatagtact     300
cc                                                                    302
```

<210> SEQ ID NO 15
<211> LENGTH: 442
<212> TYPE: DNA
<213> ORGANISM: Homo sapiens

<400> SEQUENCE: 15

```
accatcaact gcaagtccag ccagagtgtt ttgtacactt ccagcaataa gaactactta      60
gcttggtacc agcagaaacc aggacagcct cctaaactac tcatttactg ggcatctacc     120
cgggaatccg gggtccctga ccgattcagt ggcagcgggt ctgggacaga tttcactctc     180
accatccgca gcctgcaggc tgaagatgtg cagtttatt actgtcagca atattatact     240
attccattca atttcggccc tgggaccaga gtggatatca aacgaactgt ggctgcacca     300
```

-continued

| | |
|---|---|
| tctgtcttca tcttcccgcc atctgatgag cagttgaaat ctggaactgc ctctgttgtg | 360 |
| tgcctgctga ataacttcta tcccagagag gccaaagtac agtggaaggt ggataacgcc | 420 |
| ctccaatcgg gttggggaaa aa | 442 |

<210> SEQ ID NO 16
<211> LENGTH: 38
<212> TYPE: DNA
<213> ORGANISM: Homo sapiens

<400> SEQUENCE: 16

| | |
|---|---|
| attcactttc ggccctggga ccaaagtgga tatcaaac | 38 |

<210> SEQ ID NO 17
<211> LENGTH: 149
<212> TYPE: DNA
<213> ORGANISM: Homo sapiens

<400> SEQUENCE: 17

| | |
|---|---|
| gaactgtggc tgcaccatct gtcttcatct tcccgccatc tgatgagcag ttgaaatctg | 60 |
| gaactgcctc tgttgtgtgc ctgctgaata acttctatcc cagagaggcc aaagtacagt | 120 |
| ggaaggtgga taacgccctc caatcgggt | 149 |

<210> SEQ ID NO 18
<211> LENGTH: 259
<212> TYPE: DNA
<213> ORGANISM: Homo sapiens

<400> SEQUENCE: 18

| | |
|---|---|
| agaccctctc actcacctgt gccatctccg gggacagtgt ctctagcaac agtgctgctt | 60 |
| ggaactggat caggcagtcc ccatcgagag gccttgagtg gctgggaagg acatactaca | 120 |
| ggtccaagtg gtataatgat tatgcagtat ctgtgaaaag tcgaataacc atcaacccag | 180 |
| acacatccaa gaaccagttc tccctgcagc tgaactctgt gactcccgag gacacggctg | 240 |
| tgtattactg tgcaagaga | 259 |

<210> SEQ ID NO 19
<211> LENGTH: 400
<212> TYPE: DNA
<213> ORGANISM: Homo sapiens

<400> SEQUENCE: 19

| | |
|---|---|
| agaccctctc actcacctgt gccatctccg gggacagtgt ctctagcgac agtgctgctt | 60 |
| ggaactggat caggcagtcc ccatcgagag gccttgagtg gctgggaagg acatactaca | 120 |
| ggtccaagtg gtataatgat tatgcagttt ctgtgaaaag tcgaataacc atcaacccag | 180 |
| acacatccaa gaaccagttc tccctgcagc tgaactctgt gactcccgag gacacggctg | 240 |
| tgtattactg tgcaagagat atagcagtgg ctggcgtcct ctttgactgc tggggccagg | 300 |
| gaaccctggt caccgtctcc tcagggagtg catccgcccc aaccttttc cccctcgtct | 360 |
| cctgtgagaa ttccccgtcg gatacgagca gcgtggccgt | 400 |

<210> SEQ ID NO 20
<211> LENGTH: 43
<212> TYPE: DNA
<213> ORGANISM: Homo sapiens

<400> SEQUENCE: 20

| | |
|---|---|
| ctttgactac tggggccaag gaaccctggt caccgtctcc tca | 43 |

```
<210> SEQ ID NO 21
<211> LENGTH: 15
<212> TYPE: DNA
<213> ORGANISM: Homo sapiens

<400> SEQUENCE: 21
tatagcagca gctgg                                                      15

<210> SEQ ID NO 22
<211> LENGTH: 77
<212> TYPE: DNA
<213> ORGANISM: Homo sapiens

<400> SEQUENCE: 22
gggagtgcat ccgccccaac ccttttcccc ctcgtctcct gtgagaattc cccgtcggat     60
acgagcagcg tggccgt                                                    77
```